US009441041B2

(12) United States Patent
Arthos et al.

(10) Patent No.: US 9,441,041 B2
(45) Date of Patent: Sep. 13, 2016

(54) USE OF ANTAGONISTS OF THE INTERACTION BETWEEN HIV GP120 AND α4β7 INTEGRIN

(71) Applicant: The United States of America, as Represented by the Secretary, Department of Health and Human Services, Washington, DC (US)

(72) Inventors: James Arthos, Rockville, MD (US); Diana Goode, Bellingham, MA (US); Claudia Cicala, Bethesda, MD (US); Anthony S. Fauci, Washington, DC (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/859,675

(22) Filed: Sep. 21, 2015

(65) Prior Publication Data

US 2016/0075786 A1 Mar. 17, 2016

Related U.S. Application Data

(62) Division of application No. 12/518,035, filed as application No. PCT/US2007/086663 on Dec. 6, 2007, now Pat. No. 9,193,790.

(60) Provisional application No. 60/873,884, filed on Dec. 7, 2006, provisional application No. 60/920,880, filed on Mar. 30, 2007, provisional application No. 60/957,140, filed on Aug. 21, 2007.

(51) Int. Cl.
*A61K 39/00* (2006.01)
*A61K 38/12* (2006.01)
*C07K 16/28* (2006.01)
*G01N 33/569* (2006.01)

(52) U.S. Cl.
CPC ........... *C07K 16/2842* (2013.01); *A61K 38/12* (2013.01); *C07K 16/2839* (2013.01); *G01N 33/56988* (2013.01); *A61K 2039/505* (2013.01); *C07K 2317/76* (2013.01); *G01N 2333/7055* (2013.01); *G01N 2333/70503* (2013.01); *G01N 2333/70553* (2013.01); *G01N 2500/02* (2013.01); *G01N 2500/10* (2013.01)

(58) Field of Classification Search
None
See application file for complete search history.

(56) References Cited

U.S. PATENT DOCUMENTS

| 7,807,167 B2 | 10/2010 | Taylor et al. |
| 2006/0093601 A1 | 5/2006 | Fong et al. |
| 2011/0293521 A1 | 12/2011 | Hyde et al. |

FOREIGN PATENT DOCUMENTS

| AU | 2003203742 | 11/2004 |
| WO | WO 9600581 | 1/1996 |
| WO | WO 96/31602 | 10/1996 |
| WO | WO 0192549 | 12/2001 |
| WO | WO 03/072040 A2 | 9/2003 |
| WO | WO 03/072040 A3 | 9/2003 |
| WO | WO 2006/026759 | 3/2006 |

OTHER PUBLICATIONS

Ansari et al., Blocking of α4β7 gut-homing integrin during acute infection leads to decreased plasma and gastrointestinal tissue viral loads in simian immunodeficiency virus-infected rhesus macaques, *J Immunol*, 186(2):1044-59, Jan. 2011, Epub Dec. 13, 2010.
Arthos et al., "HIV-1 envelope protein binds to and signals through integrin α4β7, the gut mucosal homing receptor for peripheral T cells", *Nature*, vol. 9, No. 3, pp. 301-309, 2008.
Berger and Houff, "Progressive multifocal leukoencephalopathy: lessons from Aids and natalizumab", *Neurological Research*, vol. 28, pp. 299-305, 2006.
Berger, "Natalizumab and progressive multifocal leucoencephalopaty", *Ann. Rheum. Dis*, vol. 65, pp. 48-53, 2006.
Bhat et al., "Galactosyl Ceramide or a Derivative is an Essential Component of the Neural Receptor for Human Immunodeficiency Virus Type 1 Envelope Glycoprotein gp120", *PNAS*, vol. 88, pp. 7131-7134, 1991.
Borghi et al., "Interaction between chronically HIV-infected promonocytic cells and human umbilical vein endothelial cells: role of proinflammatory cytokines and chemokines in viral expression modulation", *Clinical and Experimental Immunology*, vol. 120, pp. 93-100, 2000.
Cicala et al., "The Integrin alpha4beta7 forms a complex with cell0surface CD4 and defines a T-cell subset that is highly susceptible to infection by HIV-1," *Proc. Natl Acad Sci USA*, (49):20877-82, Dec. 8, 2009. (Epub Nov. 20, 2009).
Cummins et al., "In Vitro Exposure to Highly Cytopathic HIV-1 X4 Strains Increases Expression of Mucosa-Associated Integrins on CD41 T Cells," *Virology*, 280, 262-272, 2001.

(Continued)

*Primary Examiner* — Nick Zou
(74) *Attorney, Agent, or Firm* — Klarquist Sparkman, LLP

(57) ABSTRACT

Methods are provided for the treatment of a HIV infection. The methods can include administering to a subject with an HIV infection a therapeutically effective amount of an agent that interferes with the interaction of gp120 and α4 integrin, such as a α4β1 or α4β7 integrin antagonist, thereby treating the HIV infection. In several examples, the α4 integrin antagonist is a monoclonal antibody that specifically binds to a α4, β1 or β7 integrin subunit or a cyclic hexapeptide with the amino acid sequence of CWLDVC. Methods are also provided to reduce HIV replication or infection. The methods include contacting a cell with an effective amount of an agent that interferes with the interaction of gp120 and α4 integrin, such as a α4β1 or α4β7 integrin antagonist. Moreover, methods are provided for determining if an agent is useful to treat HIV.

12 Claims, 14 Drawing Sheets

(56) References Cited

OTHER PUBLICATIONS

Davidson et al., "Modulation of integrin function inhibits HIV transmission to epithelial cells and fertilization," *J. Reprod Immunol.*, 41(1-2):271-90, Dec. 1998.

Douglas et al., "Effect of cytokines and anti-adhesion molecule antibodies on the adhesion of lymphocytic cells to human syncytiotrophoblast", *Journal of Reproductive Immunology*, vol. 24, pp. 49-62, 1994.

Freshney, *Culture of Animal Cells, A Manual of Basic Technique*, Alan R. Liss, Inc., New York, p. 4, 1983.

Gonzalez-Amaro et al., "Therapeutic anti0integrin (alpha4 and alphaL) monoclonal antibodies: two-edged swords?," *Immunology*, 116(3):289-06, Nov. 2005.

Guadalupe et al., "Severe CD4+ T-cell depletion in gut lymphoid tissue during primary human immunodeficiency virus type 1 infection and substantial delay in restoration following highly active antiretroviral therapy," *J Virol*, 77(21):11708-17, Nov. 2003.

Hernandez-Caselles et al., "Specific regulation of VLA-4 and alpha 4 beta 7 integrin expression on human activated T lymphocytes", Abstract Only, *Journal of Immunology*, vol. 156, No. 10, pp. 3668-3677, 1996.

Jackson, "Alpha 4 Integrin Antagonists", *Current Pharmaceutical Design*, vol. 8, pp. 1229-1253, 2002.

Jolly and Sattentau, "Retroviral Spread by Induction of Virological Synapses", *Traffic*, vol. 5, pp. 643-650, 2004.

Kleinschmidt-Demasters and Tyler, "Progressive Multifocal Leukoencephalopathy Complicating Treatment with Natalizumab and Interferon Beta-1a for Multiple Sclerosis", *New England Journal of Medicine*, vol. 353, No. 4, pp. 369-374, 2005.

Krieg et al., "Gut-homing ($\alpha_4\beta_{7+}$) Th1 memory responses after inactivated poliovirus immunization in poliovirus orally pre-immunized donors", *Journal of General Virology*, vol. 85, pp. 1571-1579, 2004.

Krzysiek et al., "Preferential and persistent depletion of CCR5+ T-helper lymphocytes with nonlymphoid homing potential despite early treatment of primary HIV infection", *Blood*, vol. 98, No. 10, pp. 3169-3171, 2001.

LaFrenie et al., "Involvement of Integrin $\alpha v\beta 3$ in the Pathogenesis of Human Immunodeficiency Virus Type 1 Infection in Monocytes", *Virology*, vol. 297, pp. 31-38, 2002.

Lehmann et al., "Expression of the integrin alpha Ebeta 7 identifies unique subsets of CD25+ as well as CD25-regulatory T Cells", *PNAS*, vol. 99, pp. 13031-13036, 2002.

Liao et al., "Increased Infectivity of HIV Type 1 Particles Bound to Cell Surface and Solid-Phase ICAM-1 and VCAM-1 through Acquired Adhesion Molecules LFA-1 and VLA-4", *AIDS Research and Human Retroviruses*, vol. 16, No. 4, pp. 355-366, 2000.

Lima et al., "New features of progressive multifocal leukoencephalopahty in the era of highly active antiretroviral therapy and natalizumab," *J. Neurovirol.*, 11 Suppl. 3:52-7, 2005.

Maher et al., "HIV binding, penetration, and primary infection in human cervicovaginal tissue", *PNAS*, vol. 102, No. 32, pp. 11504-11509, 2005.

McIntyre et al., "Regulation of Human T Lymphocyte Coactivation with an $\alpha 4$ Integrin Antagonist Peptide", *Journal of Immunology*, vol. 158, No. 9, pp. 4180-4186, 1997.

Moyano et al., "Cooperative role for activated alpha4 beta1 integrin and chondroitin sulfate proteoglycans in cell adhesion to the heparin III domain of fibronectin. Identification of a novel heparin and cell binding sequence in repeat III5," *J Biol Chem*, 1;274(1):135-42, Jan. 1999.

Park et al., "The use of one-bead one-compound combinatorial library method to identify peptide ligands for $\alpha 4\beta 1$ integrin receptor in non-Hodgkin's lyphoma", *Letters in Peptide Science*, vol. 8, pp. 171-178, 2002.

Perez et al., Envelope Glycoprotein Binding to the Integrin $\alpha 4\beta 7$ Is Not a General Property of Most HIV-1 Strains, *J Virol*, 88(18):10767-77, Sep. 15, 2014, Epub Jul. 9, 2014.

Rojas et al., "Human rotavirus specific T cells: quantification by ELISPOT and expression of homing receptors on CD4+ T cells," *Virology*, 314, 671-679, 2003.

Shacklett et al., "Trafficking of human immunodeficiency virus type 1-specific CD8+ T cells to gut-associated lymphoid tissue during chronic infection," *J. Virol*, 77(10):5621-31, May 2003.

Shotton et al., "Identification and Characterization of Monoclonal Antibodies Specific for Polymorphic Antigenic Determinants within the V2 Region of the Human Immunodeficiency Virus Type 1 Envelope Glycoprotein", *Journal of Virology*, vol. 69, No. 1, pp. 222-230, 1995.

Steinman, "Blocking Adhesion Molecules As Therapy for Multiple Sclerosis: Natalizumab", *Nature*, vol. 4, pp. 510-519, 2005.

Stüve et al., "Altered CD4+/CD8+T-Cell Ratios in Cerebrospinal Fluid of Natalizumab-Treated Patients With Multiple Sclerosis", *Arch. Neurol.*, vol. 63, pp. 1383-1387, 2006.

Urbinati et al., "Integrin $\alpha_v\beta_3$ as a Target for Blocking HIV-1 Tat-Induced Endothelial Cell Activation In Vitro and Angiogenesis In Vivo", *Arterioscler Thromb Vasc. Bio.*, vol. 25, No. 11, pp. 2315-2320, 2005.

Vanderslice et al., "A Cyclic Hexapeptide Is a Potent Antagonist of $\alpha_4$ Integrins", *Journal of Immunology*, vol. 158, pp. 1710-1718, 1997.

Von Andrian et al., Alpha4 integrins as therapeutic targets in autoimmune disease, *N Engl J Med*, 2;348(1):68-72, Jan. 2003.

Waldman et al., "Absence of $\beta 7$ integrin results in less graft-versus-host disease because of decreased homing of alloreactive T cells to intestine", *Blood*, vol. 107, No. 4, pp. 1703-1711, 2006.

Yousry et al., "Evaluation of Patients Treated with Natalizumab for Progressive Multifocal Leukoencephalopathy", *New England Journal of Medicine*, vol. 354, No. 9, pp. 924-933, 2006.

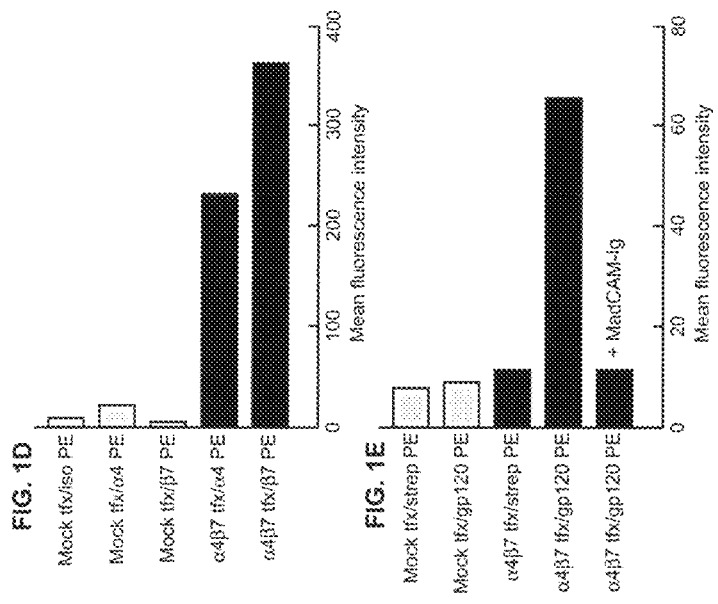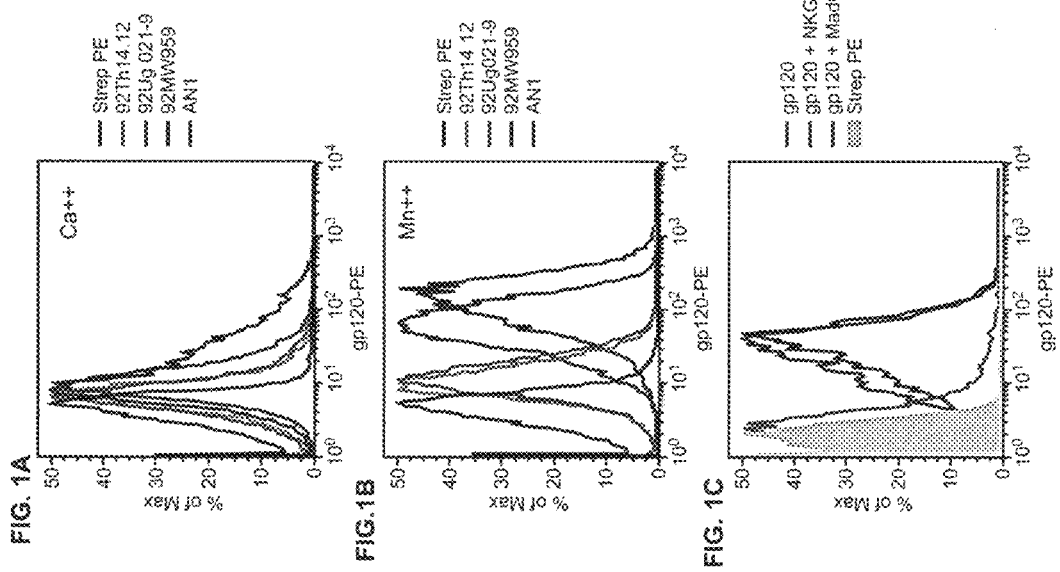
FIGS. 1A-1E

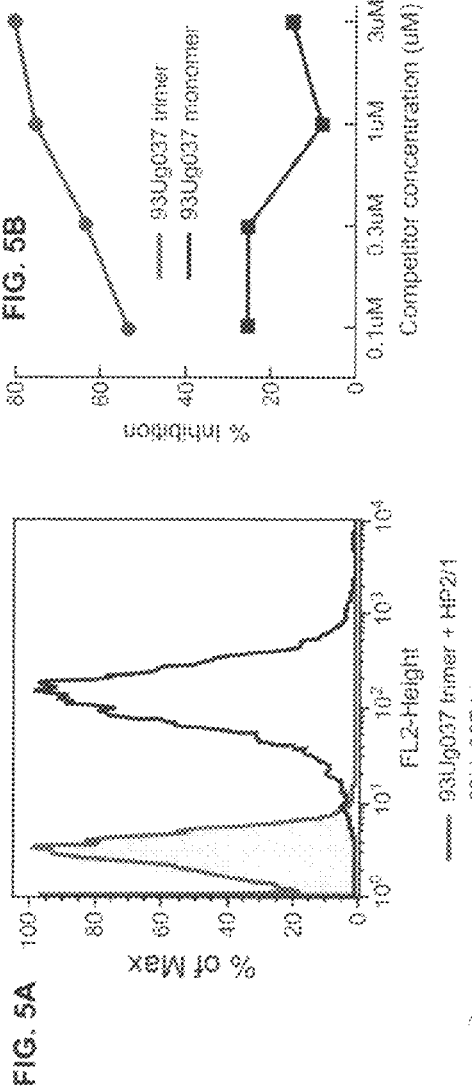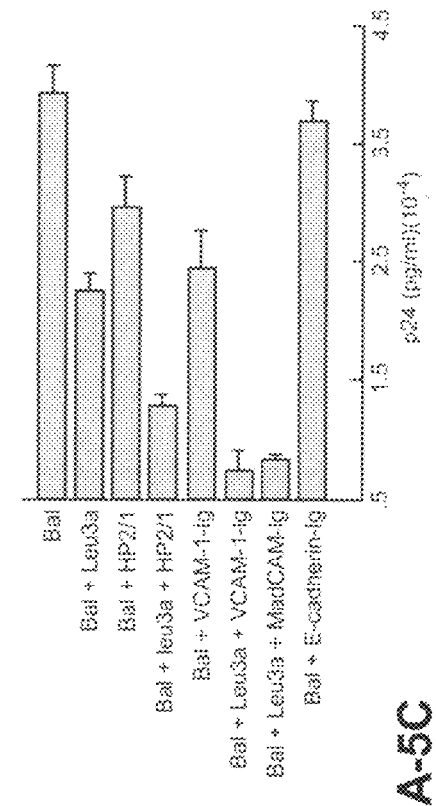
FIGS 5A-5C

```
                                                                          SEQ ID NO: 32
HXB2:         156  CSFNISTSIRGKVQKEYAFFYKLDIIPIDNDTTSYSLTSC 198
CONSENSUS:         CSFNITTSIRDKKKKVYALFYKLDVVPID-DNNSYRLINC
CONSENSUS A1                                  LDV
CONSENSUS A2                                  LDV                        SEQ ID NO: 33
CONSENSUS B                                   LDV
CONSENSUS C                                   LDI
CONSENSUS D                                   LDV
CONSENSUS F1                                  LDI
CONSENSUS F2                                  LDV
CONSENSUS G                                   LDV
CONSENSUS H                                   LDV
-----------------------------------------------------------
ANCESTRAL A1                                  LDV
ANCESTRAL B                                   LDV
ANCESTRAL C                                   LDI

CONSENSUS 0                                   DLV/M

CONSENSUS SIVsmm                              DLV
MM251                                         DLV
MM239                                         DLV
smmPBj1.9                                     DLV
smmH9                                         DLV
smmB670                                       DLI

STM                                           DLI

CPZGAB                                        DLV
CPZANT                                        DLM
CPZCAM5                                       DIV
CPZCAM3                                       DLV

CONSENSUS HIV-2                               KDV
ROD                                           KDV
ST                                            KDV
BEN                                           LEDV
```

FIG. 9B

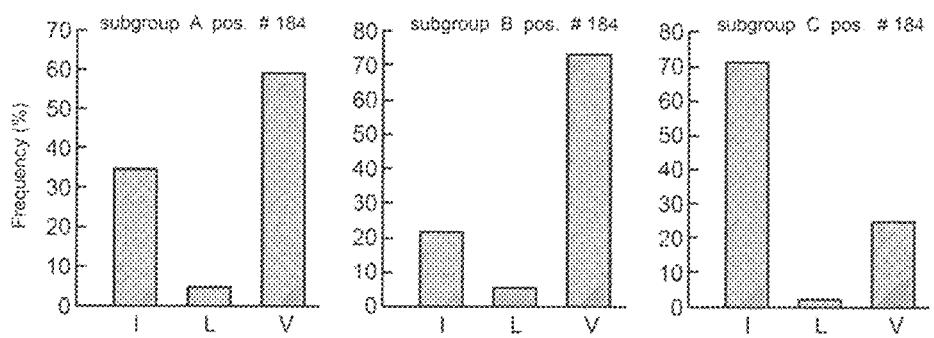

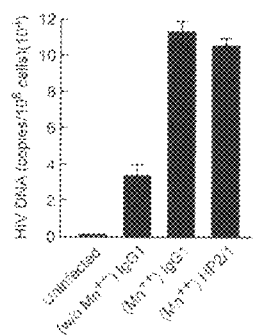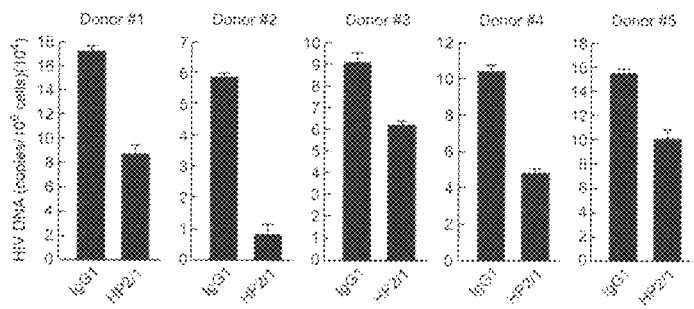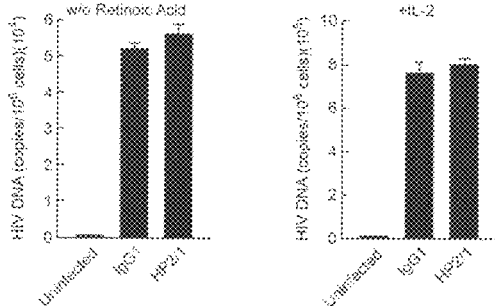
FIGS 14A-14D ered in England

USE OF ANTAGONISTS OF THE INTERACTION BETWEEN HIV GP120 AND α4β7 INTEGRIN

CROSS REFERENCE TO RELATED APPLICATIONS

This is a divisional U.S. patent application Ser. No. 12/518,035, filed Dec. 8, 2010, which is the §371 U.S. National Stage International Application No. PCT/US 2007/086663 filed Dec. 6, 2007, which was published in England under PCT Article 21(2), which in turn claims the benefit of U.S. Provisional Application No. 60/873,884, filed Dec. 7, 2006, U.S. Provisional Application No. 60/920,880, filed Mar. 30, 2007, and U.S. Provisional Application No 60/957,140 filed Aug. 21, 2007, all three provisional applications are incorporated herein by reference in their entirety.

FIELD

This relates to the field of human immunodeficiency virus (HIV), specifically to the use of α4 integrin antagonists for the treatment of HIV infections.

BACKGROUND

The primary immunologic abnormality resulting from infection by human immunodeficiency virus (HIV) is the progressive depletion and functional impairment of T lymphocytes expressing the CD4 cell surface glycoprotein. The loss of CD4 helper/inducer T cell function probably underlies the profound defects in cellular and humoral immunity leading to the opportunistic infections and malignancies characteristic of the acquired immunodeficiency syndrome (AIDS) (Lane et al., *Ann. Rev. Immunol.*, 3: 477, 1985). Studies of HIV-1 infection of fractionated CD4 and CD8 T-cells from normal donors and AIDS patients have revealed that depletion of CD4 T-cells results from the ability of HIV-1 to selectively infect, replicate in, and ultimately destroy this T lymphocyte subset (Klatzmann et al., *Science*, 225: 59, 1984).

The widespread use of highly active antiretroviral therapy (HAART) has dramatically improved the clinical course for many individuals infected with HIV (Berrey et al., *J. Infect. Dis.*, 183, (10): 1466, 2001). However, toxicities associated with long term HAART have put a high priority on the design and development of less toxic therapies. Another antiviral inhibitor is T-20 (Wild et al., *Proc. Natl. Acad. Sci. U.S.A.*, 91, No. 26: 12676, 1994; Wild et al., *Proc. Natl. Acad. Sci. U.S.A.* 89, No. 21: 10537, 1992), a relatively non-toxic peptide that disrupts viral fusion thereby protecting CD4+ lymphocytes from de novo infection. In clinical trials, T-20 has been shown to reduce plasma viral load by up to two logs (Kilby et al., *Nat. Med.*, 4, No. 11: 1302, 1998).

The strategy underlying these CD4 based therapies, i.e. blocking the interaction between gp120 and the CD4 receptor, encompasses advantages distinct from current HAART regimens. The CD4 binding site on gp120 includes highly conserved residues; thus, agents targeting this site are unlikely to encounter resistance mutants. Additionally, such agents, by blocking de novo infection, may prevent the expansion of viral reservoirs.

Monomeric soluble CD4 (sCD4) was one of the first reagents in this group to be tested clinically (Schooley et al., *Ann. Intern. Med.*, 112, No. 4: 247, 1990). Unfortunately, sCD4 failed to demonstrate significant antiviral activity in vivo (Id.). Among the problems inherent to sCD4 was its inability to efficiently neutralize primary isolates of HIV. Thus, sCD4 is not the therapeutic agent of choice for treating HIV. Thus, a need remains for additional agents that can be used to study HIV infection in vitro, and is of use for treating or preventing HIV replication in vivo.

SUMMARY

It is disclosed herein that the HIV-1 envelope protein gp120 binds to α4β7 integrin on CD4+ T-cells, natural killer (NK) cells and CD8+ T-cells. For example, interference with gp120 binding to α4β7 integrin reduces the efficiency of infection of suboptimally activated CD4+ T-cells. It is further disclosed that the α4β7 integrin plays a role in directing lymphocytes to the lamina propria of the gut, the primary site of HIV replication.

In several embodiments, methods are provided for the treatment of HIV infection. The methods can include administering to a subject with an HIV infection a therapeutically effective amount of an agent that interferes with the interaction of gp120 and α4 integrin, such as an α4 integrin antagonist, thereby treating the HIV infection. For example, the α4-specific integrin antagonist acts as a microbicide, in which the antagonist reduces the infectivity of HIV.

The methods can include administering to the subject a fragment of gp120 that interferes with the interaction of gp120 and α4 integrin. The methods can include administering an α4 integrin antagonist, such as an antibody, an LDV peptide, a peptidomimetic antagonist, a proteomimetic antagonist, or a small molecule antagonist. Additional agents, such as anti-viral agents, can be administered to the subject.

Methods are provided herein to reduce HIV replication. The methods include contacting a cell with an effective amount of an agent that interferes with the interaction of gp120 and α4 integrin, such as α4-specific integrin antagonist. The methods can also include contacting a cell with a fragment of gp120 that interferes with the interaction of gp120 and α4 integrin subunit. For example, the α4-specific integrin antagonist can be an antibody, a peptide antagonist, an LDV peptide, a peptidomimetic antagonist, a proteomimetic antagonist, or a small molecule antagonist. The cell can also be contacted with an effective amount of an additional agent, such as anti-viral agent. The cell can be in vivo or in vitro.

Exemplary antagonists of use include α4β7 integrin antagonists and α4β1 integrin antagonists. These antagonists include, but are not limited to, antibodies, peptide antagonists LDV peptides, peptidomimetic antagonists, proteomimetic antagonists, and small molecule antagonists. Specific exemplary α4β7 integrin antagonists include an antibody that specifically binds α4 integrin subunit, such as a humanized monoclonal antibody that specifically binds α4 integrin subunit, and an antibody that specifically binds β7 integrin subunit, such as a humanized monoclonal antibody that specifically binds β7 integrin subunit. In several examples that antibody is a humanized form of HP2/1 monoclonal antibody, humanized form of L25 monoclonal antibody, humanized form of 2B4-3 monoclonal antibody or fragments thereof. In an example, the antagonist is Natalizumab (also known as TYSABRI™ or ANTEGRIN™). Specific β7 antagonists include a humanized form of FIB504 monoclonal antibody, humanized form of FIB27 monoclonal antibody or fragments thereof. In an example, the antagonist is MLNO2 or LDP-02, humanized antibodies to α4β7 integrin.

The foregoing and other features will become more apparent from the following detailed description of several embodiments, which proceeds with reference to the accompanying figures.

BRIEF DESCRIPTION OF THE FIGURES

FIGS. 1a-1e illustrate that gp120 binds α4β7 integrin on NK cells. FIG. 1a is a histogram illustrating the flow cytometric analysis of biotinylated recombinant gp120s derived from 92Th14-12 (subgroup B), 92Ug021-9 (subgroup A), 92MW959 (subgroup C), and AN1 (a subgroup B ancestral envelope), binding to freshly isolated NK cells in the presence of $Ca^{++}$. FIG. 1b is a histogram illustrating the flow cytometric analysis of biotinylated recombinant gp120s derived from 92Th14-12 (subgroup B), 92Ug021-9 (subgroup A), 92MW959 (subgroup C), and AN1 (a subgroup B ancestral envelope), binding to freshly isolated NK cells in the presence of $Mn^{++}$. FIG. 1c is a histogram illustrating the flow cytometric analysis of the binding of biotinylated 92MW959 gp120 to NK cells in the presence of a five-fold molar excess of MadCAM-Ig or NKG2D-Ig. FIG. 1d is a bar graph illustrating the mean fluorescent intensity induced by the binding of PE-conjugated α4 and β7 integrin mAbs to 293T cells cotransfected with α4 and β7 integrin cDNAs. FIG. 1e is a bar graph illustrating the mean fluorescent intensity of biotinylated AN1 gp120 binding to the same 293T cell transfectants as in FIG. 1d in the absence or presence of a five-fold molar excess of MadCAM-Ig.

FIG. 2a is a histogram illustrating the expression of α4 integrin in the presence and absence of IL2 in cells stained with an α4 integrin subunit mAB HP2/1. FIG. 2b is a histogram illustrating the expression of β7 integrin subunit in the presence and absence of IL2 in cells stained with β7 mAb FIB504. FIG. 2c is a histogram illustrating the expression of β1 integrin subunit in the presence and absence of IL2 in cells stained with a β1 integrin subunit mAb P4G11.

FIG. 3a is a bar graph illustrating CD8-depleted OKT3/IL2 activated peripheral blood mononuclear cells (PBMCs) cultured in the presence of retinoic acid (RA), unless otherwise specified, stained with biotinylated AN1 gp120. FIG. 3b is a bar graph illustrating the same RA-treated cells as in FIG. 3a in which the cells were stained with biotinylated gp120 in the presence of Leu3A, plus either E-cadherin-Ig, MadCAM-Ig or VCAM-Ig. FIG. 3c is a bar graph illustrating the mean fluorescent intensity of RA-treated cells stained with biotinylated gp120 in the presence of Leu3A and various α4, β7, and β1 integrin monoclonal antibodies (mAbs). Binding is expressed as the percent inhibition relative to gp120-binding in the absence of integrin antibodies (defined as 100%). Error bars reflect the standard deviation obtained from three independent binding/inhibitions. FIG. 3d is a bar graph illustrating activated CD8+ T-cells cultured in the presence of RA, stained with AN1 gp120, 93MW959 gp120 or Ug21-9 gp120+/− divalent cations, and blocked with the α4 integrin mAb HP2/1 where specified. All results are representative of three or more independent studies.

FIG. 4a is a histogram illustrating inhibition of gp120 to RA-treated CD8+ T-cells by HIV+ immune serum from a subject with a viral load of 150,000 RNA copies per μL. FIG. 4b is a histogram illustrating inhibition of gp120 to RA-treated CD8+ T-cells by HIV+ immune serum from a subject with a viral load of 40,000 RNA copies per microliter.

FIGS. 5a-5c illustrate trimeric envelope and virion spikes bind to α4β7 integrin on T-cells. FIG. 5a is a histogram illustrating the effect of α4 integrin mAb HP2/1 on activated CD8+ T-cells cultured in the presence of RA stained with biotinylated 93Ug037 trimer. FIG. 5b is a graph illustrating the effect of increasing concentrations of unlabeled monomeric or trimeric 93Ug037 gp120 on activated CD8+ T-cells cultured in the presence of RA stained with biotinylated 93Ug037 trimer (0.1 micromolar) in the presence of increasing concentrations of unlabeled monomeric or trimeric 93Ug037 gp120. FIG. 5c is a bar graph illustrating the results of p24 Gag antigen ELISA of lysates from RA-treated PBMCs incubated at 4° C. with HIV-1 Bal in the presence of Mn++, with the addition of Leu3A, HP2/1, MadCAM-Ig, VCAM-1-Ig and E-cadherin-Ig where specified. Error bars represent the standard deviation from the mean of replicate samples. Significance values (two tailed paired t-test) relative to Bal+Leu3a are: Bal+Leu3A+HP2/1, p=0.03; Bal+Leu3A+VCAM-1, p=0.024; and Bal+Leu3A+MadCAM, p=0.027.

FIG. 6a is a histogram comparing 93MW959 and 92Ug21-9 gp120s binding to RA cultured PBMCs in the presence of Leu3A. Also included is 93MW959 binding the presence of Leu3A+HP2/1. FIG. 6b is a histogram comparing P5.13-59 and P5.13-53 gp120s binding to RA cultured PBMCs in the presence of Leu3A. Also included is P5.13-59 binding in the presence of Leu3A+HP2/1. FIG. 6c is a histogram illustrating SF33A2' gp120 binding to RA treated PBMCs in the absence and presence of Leu3A. FIG. 6d is a histogram illustrating SF162P3' gp120 binding to RA cultured PBMCs in the absence or presence of Leu3A or Leu3A+HP2/1. For comparison, staining of SF33A2' gp120 in the presence of Leu3A is also provided.

FIG. 7a is a histogram illustrating the binding of 92Ug21-9 gp120 to RA cultured PBMCs in the presence of Leu3A and Leu3A+MadCAM-Ig. FIG. 7b is a histogram illustrating the binding of P5.13-53 gp120 to RA cultured PBMCs in the presence of Leu3A and Leu3A+MadCam-Ig. FIG. 7c is a histogram illustrating the binding of 93MW959 gp120 to RA cultured PBMCs in the presence of Leu3A, Leu3A+MadCAM-Ig, and Leu3A+HP2/1. FIG. 7d includes a histogram illustrating the binding of 93Ug037 trimer to RA cultured PBMCs in the presence of Leu3A, Leu3A+MadCAM-Ig, Leu3+VCAM-Ig, and Leu3A+HP2/1. FIG. 7e includes a bar graph illustrating the mean fluorescence intensity in α4β7, α4β1, and α4 integrin transfected 293T cells stained with a 93UG037 trimer. FIG. 7e insets include histograms illustrating α4β7 integrin and α4β1 integrin transfected 293T cells stained with α4, β7, and α1 integrin mAbs.

FIG. 8a is a bar graph illustrating the mean fluorescent intensity of cultured CD8+ T-cells stained with biotinylated gp120 with the inclusion of the cyclic peptide CWLDVC at varying concentrations (0.19 μM-12.5 μM), or a scrambled control peptide (3.1 µM). FIG. 8b is a histogram illustrating the effect of Leu3A and HP2/1 on RA-treated PBMCs stained with biotinylated AN1 gp120. FIG. 8c is a histogram illustrating the effect of Leu3A and HP2/1 on RA-treated PBMCs stained with biotinylated AN1L182A,D183A gp120.

FIGS. 9a and 9b illustrate sequence conservation of the α4β7 integrin binding motif in the V2 loop of HIV. FIG. 9a is a table providing the V2 loops of HXB2 and a consensus sequence (consensus of all HIV-1 subgroup consensus sequences). Aligned residues 182-184 (HXB2 numbering) are presented for each of the major subgroups of HIV-1 and the corresponding residues in the ancestral sequences for subgroups A1, B, and C. Also included are the corresponding sequences for consensus HIV-1 O, consensus SIVsmm, common SIV isolates along with STM, several CPZ isolates, a consensus HIV-2 and three common HIV-2 isolates. All sequence information was obtained from the HIV Sequence Database (2006) (web address hiv-web.1an1.gov/content/hiv-db/mainpage). FIG. 9b provides a series of bar graphs illustrating the frequency (%) of the three most common residues (Ile, Leu, Val) in subgroups A, B, and C at position 184 of the V2 loop among the 976 sequences listed in the 2006 HIV Sequence Database.

Figures 2A, 2B, 2C:
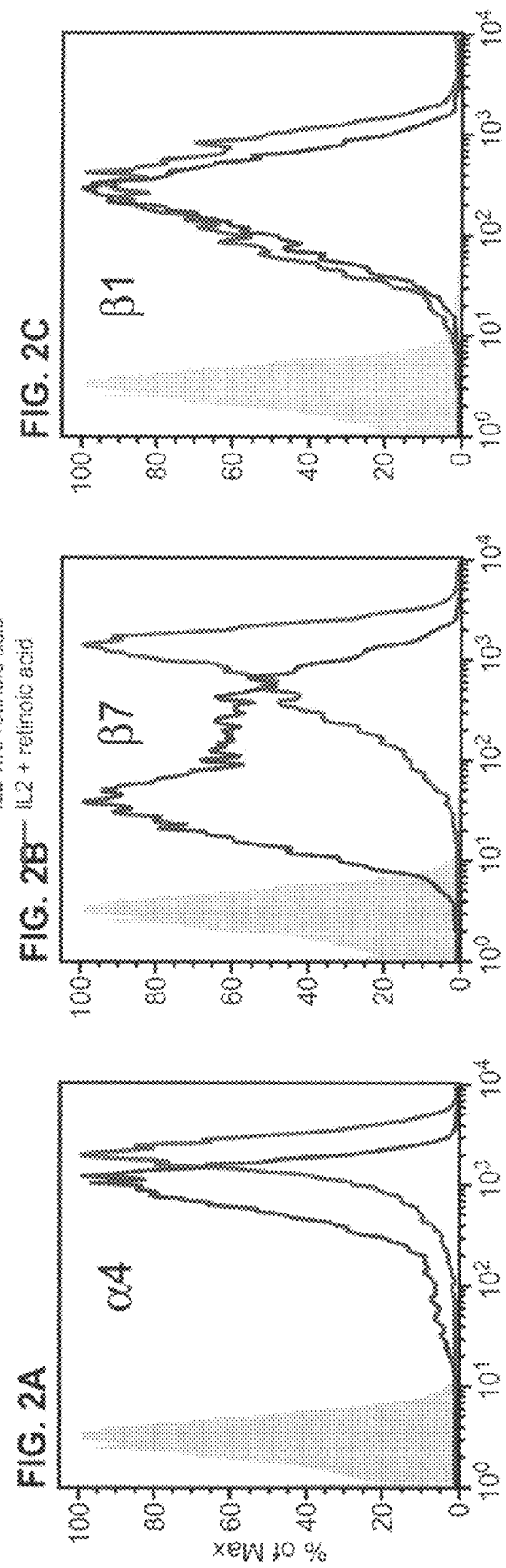
FIGS. 2a-2c illustrate retinoic acid induced expression of α4 and β7 integrin on PBMCs. PBMCs were cultured by six days in presence of OKT3 and IL2, and with retinoic acid where specified.

*Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin exempli gratia, and is used herein to indicate a non-limiting example. Thus, the abbreviation "e.g." is synonymous with the term "for example." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. In addition, the materials, methods, and examples are illustrative only and not intended to be limiting.

In order to facilitate review of the various embodiments of this disclosure, the following explanations of specific terms are provided:

Adjuvant: A vehicle used to enhance antigenicity; such as a suspension of minerals (alum, aluminum hydroxide, aluminum phosphate) on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). Adjuvants also include immunostimulatory molecules, such as cytokines, costimulatory molecules, and for example, immunostimulatory DNA or RNA molecules, such as CpG oligonucleotides.

Administration: The introduction of a composition into a subject by a chosen route. Administration can be systemic or local. For example, if the chosen route is intravenous, the composition is administered by introducing the composition into a vein of the subject, and if the chosen route is intramuscular, the compositing is administered by introducing the composition in to a muscle.

Agent: Any protein, nucleic acid molecule, compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject). In examples, an agent is a α4β7 or α4β1 integrin antagonist. In a particular example, an agent specifically inhibits the activation of the α4β7 and/or α4β1 integrin, thereby inhibiting at least one of HIV replication or HIV infection. Agents of use include a α4-specific integrin antagonist that specifically binds to a α4, β7, or β1 integrin subunit. One exemplary non-limiting agent of use is a cyclic hexapeptide with the amino acid sequence of CWLDVC (SEQ ID NO:1). Other exemplary agents of use include monoclonal antibodies that specifically bind the α4, β7 or β1 integrin subunit.

Antibody: A polypeptide substantially encoded by an immunoglobulin gene or immunoglobulin genes, or fragments thereof, which specifically binds and recognizes an analyte (antigen). In one example, the antibody specifically binds an integrin that includes the α4 integrin subunit (e.g., α4β7 or α4β1 integrin) or an antigenic fragment of the α4 integrin. Immunoglobulin genes include the kappa, lambda, alpha, gamma, delta, epsilon and mu constant region genes, as well as the myriad immunoglobulin variable region genes.

Antibodies exist, for example as intact immunoglobulins and as a number of well characterized fragments produced by digestion with various peptidases. For instance, Fabs, Fvs, and single-chain Fvs (SCFvs) that bind to an integrin subunit (α4, β7 or β1 integrin subunit) or fragments of the integrin subunit would be integrin subunit-specific binding agents. This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (such as humanized murine antibodies), heteroconjugate antibodies such as bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Functional fragments of antibodies specifically bind the antigen of interest, and include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. The term "antibody," as used herein, also includes antibody fragments either produced by the modification of whole antibodies or those synthesized de novo using recombinant DNA methodologies.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." In one example, monoclonal antibodies to the α4 integrin are employed. For example, the monoclonal antibody can be a α4 integrin subunit monoclonal antibody (such as HP2/1 monoclonal antibody, L25 monoclonal antibody or 2B4-3 monoclonal antibody) or a β7 integrin subunit monoclonal antibody (such as FIB504 monoclonal antibody or FIB27 monoclonal antibody).

Monoclonal antibodies include humanized monoclonal antibodies. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example, see U.S. Pat. No. 5,585,089). Specific examples of humanized antibodies include MLNO2 (a humanized antibody to α4β7), LDP-02 (a humanized antibody to α4β7), Antegren (a humanized monoclonal antibody against α4 integrin), and natalizumab (a humanized antibody primarily specific for α4β1 integrin).

CD4: Cluster of differentiation factor 4 polypeptide, a T-cell surface protein that mediates interaction with the MHC class II molecule. CD4 also serves as the primary receptor site for HIV on T-cells during HIV-1 infection.

The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, *Cell,* 42:93, 1985).

The term "CD4" includes polypeptide molecules that are derived from CD4 include fragments of CD4, generated either by chemical (for example enzymatic) digestion or genetic engineering means. Such a fragment may be one or more entire CD4 protein domains. The extracellular domain of CD4 consists of four contiguous immunoglobulin-like regions (D1, D2, D3, and D4, see Sakihama et al., *Proc. Natl. Acad. Sci.,* 92: 6444, 1995; U.S. Pat. No. 6,117,655), and amino acids 1 to 183 have been shown to be involved in gp120 binding. For instance, a binding molecule or binding domain derived from CD4 would comprise a sufficient portion of the CD4 protein to mediate specific and functional interaction between the binding fragment and a native or viral binding site of CD4. One such binding fragment includes both the D1 and D2 extracellular domains of CD4 (D1D2 is also a fragment of soluble CD4 or sCD4 which is comprised of D1 D2 D3 and D4), although smaller fragments may also provide specific and functional CD4-like binding. The gp120-binding site has been mapped to D1 of CD4.

CD4 polypeptides also include "CD4-derived molecules" which encompasses analogs (non-protein organic molecules), derivatives (chemically functionalized protein molecules obtained starting with the disclosed protein sequences) or mimetics (three-dimensionally similar chemicals) of the native CD4 structure, as well as proteins sequence variants or genetic alleles that maintain the ability to functionally bind to a target molecule.

Contacting: Placement in direct physical association; includes both in solid and liquid form. Contacting can occur in vitro with isolated cells or in vivo by administering the agent to a subject.

Control: A reference standard. A control can be a known value indicative of binding of a natural α4 integrin ligand, such as vascular cell adhesion molecule (VCAM) or mucosal addressin cell adhesion molecule (MadCAM) to an α4 integrin, such as an α4β1 or an α4β7 integrin. A control can also be a known value indicative of binding of a natural β1 or β7 integrin ligand to an integrin, such as an α4β1 or an α4β7 integrin.

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%.

Degenerate variant and conservative variant: A polynucleotide encoding a polypeptide or an antibody that includes a sequence that is degenerate as a result of the genetic code. For example, a polynucleotide encoding a polypeptide antagonist or a neutralizing antibody that includes a sequence, wherein the polynucleotide is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified within a protein encoding sequence, the codon can be altered to any of the corresponding codons described without altering the encoded protein. Such nucleic acid variations are "silent variations," which are one species of conservative variations. Each nucleic acid sequence herein that encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Not all residue positions within a protein will tolerate an otherwise "conservative" substitution. For instance, if an amino acid residue is essential for a function of the protein, even an otherwise conservative substitution may disrupt that activity. Thus, a conservative substitution does not alter the basic function of a protein of interest.

Detect: To determine if a molecule (such as a signal or particular nucleotide nucleic acid probe, amino acid, or protein) is present or absent. In one example, a ligand for the α4β1 or integrin α4β7 is detected. In some examples, this can further include quantification.

Epitope: An antigenic determinant. These are particular chemical groups or peptide sequences on a molecule that are antigenic, such that they elicit a specific immune response. An antibody binds a particular antigenic epitope, such as a α4, β1, or β7 integrin subunit epitope.

Expression: Translation of a nucleic acid into a protein. Proteins can be expressed and remain intracellular, can become a component of the cell surface membrane, or be can secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

gp120: The envelope protein from HIV. The envelope protein is initially synthesized as a longer precursor protein of 845-870 amino acids in size, designated gp160. Gp160 forms a homotrimer and undergoes glycosylation within the Golgi apparatus. In vivo, it is then cleaved by a cellular protease into gp120 and gp41. Gp41 contains a transmembrane domain and remains in a trimeric configuration; it interacts with gp120 in a non-covalent manner. Gp120 contains most of the external, surface-exposed, domains of the envelope glycoprotein complex, and it is gp120 which binds both to the cellular CD4 receptor and to the cellular chemokine receptors (such as CCR5).

The mature gp120 wild type polypeptides have about 500 amino acids in the primary sequence. Gp120 is heavily N-glycosylated giving rise to an apparent molecular weight of 120 kD. The polypeptide is comprised of five conserved regions (C1-C5) and five regions of high variability (V1-V5). Exemplary sequence of wt gp160 polypeptides are shown on GENBANK, for example accession numbers AAB05604 and AAD12142, as available on Sep. 6, 2007, which are incorporated herein by reference.

The gp120 core has a unique molecular structure, which comprises two domains: an "inner" domain (which faces gp41) and an "outer" domain (which is mostly exposed on the surface of the oligomeric envelope glycoprotein complex). The two gp120 domains are separated by a "bridging sheet" that is not part of either domain. The gp120 core comprises 25 beta strands, 5 alpha helices, and 10 defined loop segments.

Gp120 polypeptides also include "gp120-derived molecules" which encompasses analogs (non-protein organic molecules), derivatives (chemically functionalized protein molecules obtained starting with the disclosed protein sequences) or mimetics (three-dimensionally similar chemicals) of the native gp120 structure, as well as proteins sequence variants (such as mutants), genetic alleles, fusions proteins of gp120, or combinations thereof.

The third variable region referred to herein as the V3 loop is a loop of about 35 amino acids critical for the binding of the co-receptor and determination of which of the co-receptors will bind. In certain examples the V3 loop comprises residues 296-331.

The amino acids residues in gp120 can be numbered using the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex. which is incorporated by reference herein in its entirety.

Gut-associated lymphoid tissue (GALT): Lymphoid tissue within the gut involved in producing and storing immune cells that are involved in defending the body against infective organisms and foreign substances. The term may include the following tissues: tonsils, adenoids, Peyer's patches, lymphoid aggregates in the appendix and large intestine, lymphoid tissue accumulating with age in the stomach, small lymphoid aggregates in the oesophagus, and diffusely distributed lymphoid cells and plasma cells in the lamina propria of the gut.

HIV (human immunodeficiency virus): A retrovirus that causes immunosuppression in humans (HIV disease) and leads to a disease complex known as the acquired immunodeficiency syndrome (AIDS). "HIV disease" refers to a well-recognized constellation of signs and symptoms (including the development of opportunistic infections) in persons who are infected by an HIV virus, for example as determined by antibody or western blot studies. Laboratory findings associated with this disease include a progressive decline in T-helper cells.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Inhibit: To decrease, limit or block the action or function of a molecule. In an example, the activation of $\alpha 4\beta 1$ or $\alpha 4\beta 7$ integrin is decreased, limited or blocked by a $\alpha 4\beta 1$ or $\alpha 4\beta 7$ integrin-specific antagonist. For example, the $\alpha 4\beta 1$ or $\alpha 4\beta 7$-integrin specific antagonist inhibits activation of $\alpha 4\beta 1$ or $\alpha 4\beta 7$ integrin by gp120, thereby reducing HIV infection or HIV replication.

Inhibiting or treating a disease: Inhibiting the full development of a disease or condition, for example, in a subject who is at risk for a disease such as acquired immune deficiency syndrome (AIDS), AIDS related conditions, HIV-1 infection, or combinations thereof. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Integrin: A cell surface transmembrane glycoprotein receptor. Integrins are involved in many biological processes such as wound healing, blood clot formation, gene regulation, and immune responses. Integrins can regulate tissue specific cell adhesion molecules. Integrins are heterodimeric non-covalently associated glycoproteins composed of two subunits. The subunits, which are designated alpha and beta, have approximate molecular weights of 150-180 kilodaltons and 90-110 kilodaltons, respectively. The $\alpha 4\beta 1$ and $\alpha 4\beta 7$ integrins are involved in leukocyte migration and adhesion. The sequences for these subunits are publicly available on GenBank, see, for example Gene Accession No. NM_000885 for $\alpha 4$ integrin (also known as CD49D), Gene Accession No. NM_002211 for $\beta 1$ integrin (also known as CD29), and Gene Accession No. NM_000889 for $\beta 7$ integrin. The $\alpha 4$ integrins interact with VCAM and/or MadCAM. Monoclonal antibodies (such as TYSABRI™ or natalizuamb) have been produced that specifically bind $\alpha 4$ integrin (and can distinguish $\alpha 4$ integrins from other integrins). Antagonists of $\alpha 4$ integrins are known, and include antibodies, peptide antagonists, LDV/LDI peptides, peptidomimetic antagonists, proteomimetic antagonists, and small molecule antagonists. Exemplary $\alpha 4$ antagonists are disclosed in Jackson, *Curr. Pharm. Design* 8: 1229-1253, 2002, which is incorporated by reference herein in its entirety.

MadCAM, VCAM, and fibronectin all encode structurally homologous binding motifs that each engage $\alpha 4\beta 7$ integrin. In fibronectin this motif appears as the amino acids Leu-Asp-Val (LDV), while in VCAM-1 the amino acid sequence IDS is employed, and MadCAM utilizes the amino acid sequence LDT. Additional contacts that fall outside of these loops confer upon each of these ligands unique characteristics with respect to $\alpha 4\beta 7$ integrin recognition. $\alpha 4\beta 7$ integrin itself also encodes three LDV amino acid sequences, two of which are believed to functionally critical for activity in vivo.

Isolated: An "isolated" biological component (such as a nucleic acid, peptide or protein) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids.

$K_d$: The dissociation constant for a given interaction, such as a polypeptide ligand interaction. For example, for the bimolecular interaction of α4 integrin and gp120 it is the concentration of the individual components of the bimolecular interaction divided by the concentration of the complex.

LDI peptide: A peptide containing the Leu-Asp-Ile (LDI) integrin binding sequence. For example, an LDI peptide may be administered to inhibit HIV infection or replication by inhibiting the activation of the α4 integrin.

LDV peptide: A peptide containing the Leu-Asp-Val (LDV) integrin binding sequence, which is found in the CS-1 region of an alternately spliced fibronectin variant. For example, an LDV peptide may be administered to inhibit HIV infection or replication by inhibiting the activation of the α4 integrin. In a particular example, the LDV peptide is a cyclic hexapeptide with the amino acid sequence of CWLDVC.

Leukocyte: Cells in the blood, also termed "white blood cells," that are involved in defending the body against infective organisms and foreign substances. Leukocytes are produced in the bone marrow. There are five main types of white blood cell, subdivided between 2 main groups: polymorphonuclear leukocytes (neutrophils, eosinophils, basophils) and mononuclear leukocytes (monocytes and lymphocytes).

Ligand: Any molecule, such as VCAM or MadCAM, which specifically binds a protein, such as α4 integrin, and includes, inter alia, antibodies that specifically bind to α4 integrin. In alternative embodiments, the ligand is a protein or a small molecule (one with a molecular weight less than 6 kilodaltons).

Mimetic: A molecule (such as an organic chemical compound) that mimics the activity of an agent. Peptidomimetic and organomimetic embodiments are within the scope of this term, whereby the three-dimensional arrangement of the chemical constituents of such peptido- and organomimetics mimic the three-dimensional arrangement of the peptide backbone and component amino acid side chains in the peptide, resulting in such peptido- and organomimetics of the peptides having substantial specific activity. For computer modeling applications, a pharmacophore is an idealized, three-dimensional definition of the structural requirements for biological activity. Peptido- and organomimetics can be designed to fit each pharmacophore with computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165-174 and "Principles of Pharmacology" (ed. Munson, 1995), chapter 102 for a description of techniques used in computer assisted drug design.

Newborn infant: A human infant less than a month old.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide. In one example, a gp120 polynucleotide is a nucleic acid encoding a gp120 polypeptide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences and amino acids sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.*, 35: 351-360, 1987. The method used is similar to the method described by Higgins & Sharp, *CABIOS* 5: 151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.*, 12: 387-395, 1984).

Another example of algorithms that are suitable for determining percent sequence identity and sequence similarities are the BLAST and the BLAST 2.0 algorithm, which are described in Altschul et al., *J. Mol. Biol.*, 215: 403-410, 1990 and Altschul et al., *Nucleic Acids Res.*, 25: 3389-3402, 1977. Software for performing BLAST analyses is publicly available through the National Center for Biotechnology Information (world wide web address: ncbi.nlm.nih.gov/). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci.*, U.S.A. 89: 10915, 1989).

Another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N. Y., 2001; Tijssen, *Hybridization With Nucleic Acid Probes, Part I: Theory and Nucleic Acid Preparation, Laboratory Techniques in Biochemistry and Molecular Biology*, Elsevier Science Ltd., NY, NY, 1993 and Ausubel et al. *Short Protocols in Molecular Biology*, $4^{th}$ ed., John Wiley & Sons, Inc., 1999.

"Stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid. For example, a nucleic acid construct can include a polynucleotide sequence that hybridizes under high stringency or very high stringency, or even higher stringency conditions to a polynucleotide sequence.

Peptide Modifications: The present disclosure includes mutant peptides, as well as synthetic embodiments. In addition, analogues (non-peptide organic molecules), derivatives (chemically functionalized peptide molecules obtained starting with the disclosed peptide sequences) and variants (homologs) of peptides can be utilized in the methods described herein. The peptides disclosed herein include a sequence of amino acids that can be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell. An "anti-viral agent" or "anti-viral drug" is an agent that specifically inhibits a virus from replicating or infecting cells. Similarly, an "antiretroviral agent" is an agent that specifically inhibits a retrovirus from replicating or infecting cells.

A "therapeutically effective amount" is a quantity of a chemical composition or an anti-viral agent sufficient to achieve a desired effect in a subject being treated. For instance, this can be the amount necessary to inhibit viral replication or to measurably alter outward symptoms of the viral infection, such as increase of T cell counts in the case of an HIV-1 infection. In general, this amount will be sufficient to measurably inhibit virus (for example, HIV) replication or infectivity. When administered to a subject, a dosage will generally be used that will achieve target tissue concentrations (for example, in lymphocytes) that has been shown to achieve in vitro inhibition of viral replication.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any chain of amino acids, regardless of length or post-translational modification (such as glycosylation or phosphorylation). "Polypeptide" applies to amino acid polymers to naturally occurring amino acid polymers and non-naturally occurring amino acid polymer as well as in which one or more amino acid residue is a non-natural amino acid, for example a artificial chemical mimetic of a corresponding naturally occurring amino acid. In one embodiment, the polypeptide is a gp120 polypeptide, such as a stabilized gp120. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used interchangeably herein to refer to a polymer of amino acid residues.

Purified: The term purified does not require absolute purity; rather, it is intended as a relative term. Thus, for example, a purified protein is one in which the protein is more enriched than the protein is in its natural environment within a cell. Preferably, a preparation is purified such that the protein represents at least 50% of the protein content of the preparation.

The polypeptides or antibodies disclosed herein can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Specific Binding Agent: An agent that binds substantially or preferentially only to a defined target such as a protein, enzyme, polysaccharide, oligonucleotide, DNA, RNA, recombinant vector or a small molecule. A protein-specific binding agent binds substantially only the defined protein, or to a specific region within the protein. For example, a "specific binding agent" includes antibodies and other agents that bind substantially to a specified polypeptide, such as α4 integrin. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999). In an example, a "specific binding agent" is capable of binding to at least one of the α4, β1, or β7 integrin subunits and inhibits activation of α4β1 or α4β7 integrin thereby inhibiting HIV replication or infection.

Subject: Living multi-cellular vertebrate organisms, a category that includes human and non-human mammals. In an example, a subject is a human. In a particular example, the subject is a newborn infant. In an additional example, a subject is selected that is in need of inhibiting of an HIV infection. For example, the subject is either uninfected and at risk of HIV infection or is infected in need of treatment.

T-Cell: A white blood cell critical to the immune response. T-cells include, but are not limited to, CD4[+] T cells and CD8[+] T cells. A CD4[+] T lymphocyte is an immune cell that carries a marker on its surface known as "cluster of differentiation 4" (CD4). These cells, also known as helper T cells, help orchestrate the immune response, including antibody responses as well as killer T cell responses. CD8[+]

T-cells carry the "cluster of differentiation 8" (CD8) marker. In one embodiment, a CD8 T-cell is a cytotoxic T lymphocytes. In another embodiment, a CD8 cell is a suppressor T-cell.

Therapeutically Effective Amount: An amount of a composition that alone, or together with an additional therapeutic agent(s) (for example nucleoside/nucleotide reverse transcriptase inhibitors, a non-nucleoside reverse transcriptase inhibitors, protease inhibitors, fusion/entry inhibitors or integrase inhibitors) induces the desired response (e.g., inhibition of HIV infection or replication). In one example, a desired response is to inhibit HIV replication in a cell to which the therapy is administered. HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98%, or even at least 100% (elimination of HIV), as compared to HIV replication in the absence of the composition.

In another example, a desired response is to inhibit HIV infection. The HIV infected cells do not need to be completely eliminated for the composition to be effective. For example, a composition can decrease the number of HIV infected cells by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to the number of HIV infected cells in the absence of the composition.

A therapeutically effective amount of an agent including at least one α4β7 or α4β1 integrin antagonist, can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 µg-10 mg per 70 kg body weight if administered intravenously.

Tissue: A plurality of functionally related cells. A tissue can be a suspension, a semi-solid, or solid. Tissue includes cells collected from a subject.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Treating a disease: "Treatment" refers to a therapeutic intervention that ameliorates a sign or symptom of a disease or pathological condition, such as a sign or symptom of HIV. Treatment can also induce remission or cure of a condition, such as elimination of detectable HIV infected cells. In particular examples, treatment includes preventing a disease, for example by inhibiting the full development of a disease, such as HIV, by inhibiting HIV replication or infection or the development of AIDS. Prevention of a disease does not require a total absence of disease. For example, a decrease of at least 50% can be sufficient.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SW), and feline immunodeficiency virus (FIV). HIV-1 is a retrovirus that causes immunosuppression in humans (HIV disease), and leads to a disease complex known as AIDS. "HIV infection" refers to the process in which HIV enters macrophages and CD4+T cells by the adsorption of glycoproteins on its surface to receptors on the target cell followed by fusion of the viral envelope with the cell membrane and the release of the HIV capsid into the cell. "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T cells.

II. Methods of Treatment

It is shown herein that the HIV-1 envelope protein gp120 binds to α4β7 or α4β1 integrin on CD4+ T-cells, natural killer (NK) cells and CD8+ T-cells. Interference with gp120 binding to α4β7 integrin reduces the efficiency of infection of suboptimally activated CD4+ T-cells. Methods of treatment to reduce or inhibit HIV infection or replication are disclosed by administering to a subject with an HIV infection a therapeutically effective amount of an agent that interferes with the interaction of gp120 and α4 integrin, such as an α4β7 or α4β1 integrin-specific antagonist, thereby treating the HIV infection. The disclosed methods can be used to treat HIV-1 or HIV-2 infections. Treatment of HIV by inhibiting HIV replication or infection can include delaying the development of HIV in a subject. Treatment of a HIV also includes reducing signs or symptoms associated with the presence of HIV (for example by reducing or inhibiting HIV replication). Such inhibition can in some examples decrease or slow HIV infection by at least 10%, at least 20%, at least 50%, or at least 75%. In some examples, treatment using the methods disclosed herein prolongs the time of survival of the subject.

The methods can include administering a therapeutically effective amount of an α4β7 or α4β1 integrin-specific antagonist, such as an antibody, a peptide antagonist, an LDV/LDI peptide, a peptidomimetic antagonist, a proteomimetic antagonist, or a small molecule antagonist. In an example, the agent is a α4β7 or α4β1 integrin-specific antagonist that includes at least one of an antibody that specifically binds to a α4, β1 or β7 integrin subunit or a cyclic hexapeptide with the amino acid sequence of CWL-DVC. In a specific example, the method also includes selecting a subject that does not have multiple sclerosis or Crohn's disease. The methods can also include administering to the subject a fragment of gp120 that interferes with the interaction of full-length gp120 and α4 integrin. Additional agents can also be administered to the subject, such as anti-viral agents.

III. Method of Inhibiting HIV Infection or Replication

Methods are provided herein for inhibiting HIV infection, HIV replication or a combination thereof by administering a therapeutic effect amount of agent including at least one α4β1 or α4β7-specific integrin antagonists. The method can inhibit infection either in vitro or in vivo. When inhibiting infection in vivo, the agent can be used either to avoid infection in an HIV-seronegative subject, or to treat existing infection in an HIV-seropositive subject. The HIV-seropositive agent may or may not carry a diagnosis of AIDS. Hence in some embodiments the method involves selecting a subject in need of the agent, and administering to the subject.

In an example, HIV infection can be reduced or inhibited by contacting a cell with an effective amount of an agent including an α4β1 or α4β7-specific integrin antagonist (such as an antibody, a peptide antagonist, an LDV/LDI peptide, a peptidomimetic antagonist, a proteomimetic antagonist, a small molecule antagonist, or an siRNA). The agent specifically inhibits the activation or function of the α4β1 or α4β7 integrin and thereby reduces or inhibits HIV infection. The method can include contacting a cell with a fragment of gp120 that interferes with the interaction of gp120 and α4β1 or α4β7 integrin.

HIV infection does not need to be completely eliminated for the composition to be effective. For example, a composition can decrease HIV infection by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to HIV infection in the absence of the composition. In example, the cell is also contacted with an effective amount of an additional agent, such as anti-viral agent. The cell can be in vivo or in vitro. In a specific example, the method inhibits HIV infection in GALT.

In additional examples, HIV replication can be reduced or inhibited by similar methods. For example, methods can include contacting a cell with an effective amount of an agent including an α4β1 or α4β7-specific integrin antagonist which specifically inhibits the activation of the α4β1 or α4β7 integrin and thereby reduces or inhibits HIV replication. The α4β1 or α4β7-specific integrin antagonist can include an antibody, a peptide antagonist, an LDV/LDI peptide, a peptidomimetic antagonist, a proteomimetic antagonist, a small molecule antagonist, or an siRNA (as described in above in detail below). The method can also include contacting a cell with a fragment of gp120 that interferes with the interaction of gp120 and α4β1 or α4β7 integrin.

HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98%, or even at least 100% (elimination of detectable HIV), as compared to HIV replication in the absence of the composition. In example, the cell is also contacted with an effective amount of an additional agent, such as anti-viral agent. The cell can be in vivo or in vitro. In a specific example, the method inhibits HIV replication in GALT.

IV. Identifying HIV Therapeutic Agents

Methods are provided herein for identifying agents to treat HIV, such as agents that reduce or inhibit HIV infection or HIV replication. In one example, the method includes contacting at least one cell with one or more test agents wherein the cell expresses at least one of a α4β1, α4β7 or αLβ2 integrin. The method can also include detecting the affinity, such as a decrease in the binding of a natural ligand of the α4β1, α4β7 or αLβ2 integrin to the α4β1, α4β7, or αLβ2 integrin relative to a control, such as the binding of one of the natural ligands in the absence of the one or more test agents. In an example, the natural ligand is at least one of MadCAM-1, VCAM-1 or I-CAM-1. In several examples, a decrease in the binding of the natural ligand of the α4β1, α4β7, or αLβ2 integrin to the α4β1, α4β7 or αLβ2 integrin relative to a control indicates that the one or more test agents is of use to treat HIV. In a particular example, the method also includes contacting the cell with HIV.

In one example, determining whether there is a decrease in binding of one or more natural ligands of the α4β1, α4β7 or αLβ2 integrin to the α4β1, α4β7, or αLβ2 integrin is by use of an in vitro assay. For example, an in vitro assay can be employed to compare activity one or more such natural ligands in the presence and absence of the one or more test agents. Various types of in vitro assays may be employed to identify agents to treat HIV including, but not limited to HIV-infection assays (such as an HIV entry assay, HIV cell-to-cell spread assay), LFA-activity assay, binding assays, HIV viral synapses inhibitory assays and other well known assays to those of skill in the art.

Therapeutic Agents

Therapeutic agents are agents that when administered in therapeutically effective amounts induce the desired response (e.g., treatment of HIV). In one example, therapeutic agents bind with higher affinity to a molecule of interest, such as α4β1 or α4β7 integrin, than to other molecules. For example, a therapeutic agent can be an α4β1 or α4β7 integrin-specific antagonist that binds with high affinity to one of the integrin subunits, such as α4, β1 or β7 integrin subunit, but does not substantially bind to other integrin subunits. For example, the α4β1 or α4β7 integrin-specific antagonist binds to α4, β1 or β7 integrin subunits with a binding affinity in the range of 0.1 to 20 nM (such as 0.1 to 1 nM, 1 to 10 nM, 5 to 10 nM, or 10 to 20 nM) and reduces or inhibits the activity of such subunit.

Examples of α4β1 or α4β7 integrin-specific antagonists include antibodies, ligands, recombinant proteins, peptide mimetics, soluble receptor fragments and siRNAs. One example of a α4β1 or α4β7-specific integrin antagonist is an antibody, such as a monoclonal or polyclonal antibody. Another example, is an LDV/LDI peptide or peptidomimetic or proteomimetic antagonist. In a further example, small molecular weight inhibitors or antagonists of the receptor protein can be used as α4β1 or α4β7-specific integrin antagonists.

The following therapeutic agents are of use in the methods disclosed herein:

A. Antibodies

In particular examples, the agent is an antagonist such as an antibody that specifically binds to the α4, β1 or β7 integrin subunit. One of ordinary skill in the art can readily generate antibodies that reduce or inhibit the binding of gp120 to α4β1 or α4β7 integrin. These antibodies can be monoclonal or polyclonal. They can be chimeric or humanized. Any functional fragment or derivative of an antibody can be used including Fab, Fab', Fab2, Fab'2, and single chain variable regions. So long as the fragment or derivative retains specificity of binding for one of the α4, β1 or β7 integrin subunits and inhibit gp120 binding to such subunit it can be used in the methods provided herein. Antibodies can be tested for specificity of binding by comparing binding to appropriate antigen to binding to irrelevant antigen or antigen mixture under a given set of conditions. If the antibody binds to appropriate antigen at least 2, at least 5, at least 7 or 10 times more than to irrelevant antigen or antigen mixture, then it is considered to be specific.

In an example, monoclonal antibodies are generated to α4, β1 or β7 integrin subunits. These monoclonal antibodies each include a variable heavy ($V_H$) and a variable light ($V_L$) chain and specifically bind to one of α4, β1 or β7 integrin subunits. For example, the antibody can bind to a specific subunit with an affinity constant of at least $10^6\ M^{-1}$, such as at least $10^7\ M^{-1}$, at least $10^8\ M^{-1}$, at least $5\times10^8 M^{-1}$, or at least $10^9\ M^{-1}$.

The specific antibodies can include a $V_L$ polypeptide having amino acid sequences of the complementarity determining regions (CDRs) that are at least about 90% identical, such as at least about 95%, at least about 98%, or at least about 99% identical to the amino acid sequences of the specific integrin subunits and a $V_H$ polypeptide having amino acid sequences of the CDRs that are at least about 90% identical, such as at least about 95%, at least about 98%, or at least about 99% identical to the amino acid sequences of the specific integrin subunits.

In one example, the sequence of the specificity determining regions of each CDR is determined. Residues that are outside the SDR (non-ligand contacting sites) are substituted. For example, in any of the CDR sequences, at most one, two or three amino acids can be substituted. The production of chimeric antibodies, which include a framework region from one antibody and the CDRs from a different antibody, is well known in the art. For example, humanized antibodies can be routinely produced. The antibody or antibody fragment can be a humanized immunoglobulin having CDRs from a donor monoclonal antibody that binds a α4, β1 or β7 integrin subunit and immunoglobulin and heavy and light chain variable region frameworks from human acceptor immunoglobulin heavy and light chain frameworks. Generally, the humanized immunoglobulin specifically binds to α4, β1 or β7 integrin subunit with an affinity constant of at least $10^7\ M^{-1}$, such as at least $10^8\ M^{-1}$ at least $5\times10^8\ M^{-1}$ or at least $10^9\ M^{-1}$.

In another example, human monoclonal antibodies to α4, β1 or β7 integrin subunits are produced and used. Human monoclonal antibodies can be produced by transferring donor complementarity determining regions (CDRs) from heavy and light variable chains of the donor mouse immunoglobulin into a human variable domain, and then substituting human residues in the framework regions when required to retain affinity. The use of antibody components derived from humanized monoclonal antibodies can obviate potential problems associated with the immunogenicity of the constant regions of the donor antibody. For example, when mouse monoclonal antibodies are used therapeutically, the development of human anti-mouse antibodies (HAMA) leads to clearance of the murine monoclonal antibodies and other possible adverse events. Chimeric monoclonal antibodies, with human constant regions, humanized monoclonal antibodies, retaining only murine CDRs, and "fully human" monoclonal antibodies made from phage libraries or transgenic mice have all been used to reduce or eliminate the murine content of therapeutic monoclonal antibodies.

Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150: 2844, 1993. The antibody may be of any isotype, but in some embodiments the antibody is an IgG, including but not limited to, $IgG_1$, $IgG_2$, $IgG_3$ and $IgG_4$.

In one example, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 99% or at least about 95%, identical to the sequence of the donor immunoglobulin heavy chain variable region framework. Human framework regions, and mutations that can be made in a humanized antibody framework regions, are known in the art (see, for example, in U.S. Pat. No. 5,585,089).

Antibodies, such as murine monoclonal antibodies, chimeric antibodies, and humanized antibodies, include full length molecules as well as fragments thereof, such as Fab, $F(ab')_2$, and Fv, which include a heavy chain and light chain variable region and are capable of binding the epitopic determinant. These antibody fragments retain some ability to selectively bind with their antigen or receptor. These fragments include: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) $(Fab')_2$, the fragment of the antibody that can be obtained by treating whole antibody with the enzyme pepsin without subsequent reduction; $F(ab')_2$ is a dimer of two Fab' fragments held together by two disulfide bonds; (4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule. Methods of making these fragments are known in the art (see for example, Harlow and Lane, *Antibodies: A Laboratory Manual*, Cold Spring Harbor Laboratory, New York, 1988). Fv antibodies are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments include $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing scFvs are known in the art (see Whitlow et al., Methods: a Companion to Methods in Enzymology, Vol. 2, page 97, 1991; Bird et al., Science 242:423, 1988; U.S. Pat. No. 4,946,778; Pack et al., Bio/Technology 11:1271, 1993; and Sandhu, supra).

Antibody fragments can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., Arch. Biochem. Biophys. 89:230, 1960; Porter, Biochem. J. 73:119, 1959; Edelman et al., Methods in Enzymology, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another: Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Antibodies can also be obtained from commercial sources as detailed in Current Pharmaceutical Design 8: 1229-1253, 2002 which is hereby incorporated by reference in its entirety. For example, antibodies are commercially available for α4, β1 or β7 integrin subunit including a humanized monoclonal antibody against α4 integrin (natalizumab, also known as TYSABRI™, from Biogen/ELAN Pharmaceuticals) and humanized monoclonal antibodies against α4β7 integrin (LDP-02, available from Millennium). For example, agent can include a α4 integrin subunit monoclonal antibody, such as a humanized form of HP2/1 monoclonal antibody, humanized form of L25 monoclonal antibody, humanized form of B4-3 monoclonal antibody or fragments thereof. In other examples, the agent can include a β7 integrin subunit monoclonal antibody, such as a humanized form of FIB504 monoclonal antibody, humanized form of FIB27 monoclonal antibody or fragments thereof. In further examples, the agent includes a humanized monoclonal antibodies to α4β7 integrin (MLNO2 or LDP-02) or natalizumab (a humanized monoclonal antibody specific for α4β1 with some reactivity with α4β7).

B. LDV/LDI Peptides

In particular examples, peptides may be used to inhibit α4β1 or α47 integrin. For example, an agent comprising an LDV or LDI peptide may be administered to inhibit HIV infection or replication and thereby treat HIV. LDV and LDI peptides, which specifically bind to α4β1 or α47 integrin, can be generated by methods known in the art.

In an example, an LDV peptide includes at least a portion of the connecting segment of fibronectin (CS-1) known to be involved in lymphocyte adhesion processes through interaction with α4β1 (Springer, Cell, 76: 301, 1994), or a peptide substantially homologous to it. For example, peptides which span the 25 residue CS-1 sequence may be used (Table 1). In a specific example, the peptide includes the sequence CWLDVC (SEQ ID NO:1), which has been demonstrated to inhibit α4 integrin subunit binding to fibronectin, VCAM and MadCAM. Other examples of LDV based peptide antagonists include head to tail cyclic amides containing the general sequence Ac-(x)LDV(X)—CO (SEQ ID NO:34) where x is any D amino acid and X is any amino acid (Dutta et al., J. Pept. Sci., 6: 321, 2000).

TABLE 1

Exemplary LDV peptides.

| Sequence ID NO | LDV peptide sequence |
|---|---|
| SEQ ID NO: 5 | DELPQLVTLPHPNLHGPEILDVPST |
| SEQ ID NO: 6 | DELPQLVTL |
| SEQ ID NO: 7 | LHGPEILDVPST |
| SEQ ID NO: 8 | GPEILDVPST |
| SEQ ID NO: 9 | VTLPHPNLHGPEIL |
| SEQ ID NO: 10 | VTLPHPNLHGPEILDVPST |
| SEQ ID NO: 11 | EILDVPST |
| SEQ ID NO: 12 | LDVPST |
| SEQ ID NO: 13 | EILDV |
| SEQ ID NO: 14 | LDVPS |
| SEQ ID NO: 15 | LDV-NH2 |
| SEQ ID NO: 16 | DELPQLVTLPHPNLHGPEIL |

In an example, an LDI peptide includes the sequence LTGpLDI (SEQ ID NO:17), TGpLDI (SEQ ID NO:18), GpLDI (SEQ ID NO:19), or pLDI (SEQ ID NO:20), wherein p is D-proline (Park et al., Let. Peptide. Sci. 8: 171-178, 2002). Other examples of LDI based peptide antagonists include cyclic LDI peptides, such as those disclosed in Park et al. (Let. Peptide. Sci. 8: 171-178, 2002) which is hereby incorporated by reference in its entirety. For example, exemplary cyclic LDI peptides include, but are not limited to, cMLDIc (SEQ ID NO:21), cLLDIc (SEQ ID NO:22), cNLDI (SEQ ID NO:23), cYLDIc (SEQ ID NO:24), cGYLDIc (SEQ ID NO:25), cAWLDIc (SEQ ID NO:26), cLDIGDc (SEQ ID NO:27), and cLDIHPc (SEQ ID NO:28), wherein c is D-cysteine.

C. Peptidomimetic and Proteomimetic Antagonists

In specific examples, peptidomimetic or proteomimetic antagonists may be used to inhibit α4β1 or α4β7 integrin. For example, an agent comprising a peptidomimetic or proteomimetic antagonist may be administered to inhibit HIV infection or replication and thereby treat HIV. One of ordinary skill in the art can readily generate peptidomimetic or proteomimetic antagonists for α4β1 or α4β7 integrin. In an example, the peptidomimetic antagonists are designed to mimic the CS-1 binding region of fibronectin. In one example, an agent including one of the 5000 peptidomimetic compounds directed to encompass the overall properties of fibronectin's LDV integrin binding epitope developed by Souers et al. (Bioorg. Med. Chem. Lett., 8: 2297, 1998) is employed. In another example, the proteomimetic antagonist is a cyclic octapeptide designed to mimic the IDS binding motif from VCAM (Hynes, Cell, 69: 11, 1992) with similar conformations to the VCAM CD loop. In additional examples, the proteomimetic antagonist is based on the LDT motif of human MadCAM. For example, short cyclic peptides from five to seven amino acid residues in length containing the LDT motif flanked by two cysteine residues and cyclized via disulfide oxidation can be designed. In particular, the cyclic peptide CLDTC (SEQ ID NO:29) can be employed to inhibit α4β7 integrin. In other examples, peptide cyclo-LDTApA (SEQ ID NO:30; Viney et al., J. Immunol., 157: 2488, 1996) or other similar peptides designed to share structural features with the CD-loop in MadCAM are employed. In further examples, mannose based α4β1 or α4β7 integrin inhibitors are utilized.

D. Small Molecule Inhibitors

In an example, agents including small molecule α4β1 or α4β7 integrin antagonists are used to inhibit α4β1 or α4β7 integrin and thereby reduce or inhibit HIV infection, replication or a combination thereof. Small molecule inhibitors for α4β1 or α4β7 integrin can be generated by methods known to one of skill in the art. In general, the small molecule α4β1 or α4β7 integrin antagonists can be N and/or C-substituted amino acid analogs containing natural or unnatural sidechains. In a particular example, small molecule α4β1 or α4β7 integrin antagonists include a carboxylate and hydrophobic moieties such as proline, phenylalanine or other aromatic amino acid analogs known to be binding determinants from the previously discussed peptides and peptidomimetics. In other examples, small molecule α4β1 or α4β7 integrin antagonists include phenylalanine-based α4 antagonists containing a various N-alpha substituents coupled with modifications at the para position of the benzene, such as those disclosed by Chen et al. (Bioorganic. Medicinal Chem. Let., 10: 729, 2000). In a particular example, an analog in which the N-alpha amine is acylated with N-benzyl-pyroglutamic acid is employed. In one example, the agent includes N-(2,6-dichlorobenzoyl)-2,6-dimethoxy biphenylalanine analog TR-14035 or analogs thereof in which the para position of the 2,6-dichlorobenzoyl moiety is modified (such antagonists are available from Tanabe, San Diego, Calif. and Merck, Rahway, N.J.). Other small molecule α4β1 or α4β7 integrin antagonists can include benzylated phenylalanine analogs as disclosed by Harriman et al. (Bioorg. Med. Chem. Lett., 10: 1497, 2000), such as N-(2-hydrooxy-5-nitrobenzyl) phenylalanine isopentylamide E. siRNA In one example, agents are siRNAs that can decrease or eliminate the biological activity of α4β1 or α4β7 integrin. One of ordinary skill in the art can readily generate siRNAs, which specifically bind to a nucleic acid encoding one of the α4, β1 or β7 integrin subunits. In an example, commercially available kits, such as siRNA molecule synthesizing kits from PROMEGA® (Madison, Wis.) or AMBION® (Austin, Tex.) may be used to synthesize siRNA molecules. In another example, siRNAs are obtained from commercial sources, such as from QIAGEN® Inc (Germantown, Md.), INVITROGEN® (Carlsbad, Calif.), AMBION (Austin, Tex.), DHARMACON® (Lafayette, Colo.), SIGMA-ALDRICH® (Saint Louis, Mo.) or OPENBIOSYSTEMS® (Huntsville, Ala.).

In certain examples, expression vectors are employed to express the at least one siRNA molecule. For example, siRNA molecules can be expressed within cells from eukaryotic promoters. Those skilled in the art will recognize that any nucleic acid can be expressed in eukaryotic cells using the appropriate DNA/RNA vector. The activity of such nucleic acids can be augmented by their release from the primary transcript by an enzymatic nucleic acid (Draper et al., PCT WO 93/23569, and Sullivan et al., PCT WO 94/02595).

In some examples, siRNA molecules are expressed from transcription units (see for example, Couture et al., 1996, TIG 12:510) inserted into DNA or RNA vectors. The recombinant vectors can be DNA plasmids or viral vectors. siRNA expressing viral vectors can be constructed based on, for example, but not limited to, adeno-associated virus, retrovirus, adenovirus, lentivirus or alphavirus. In another example, pol III based constructs are used to express siRNA nucleic acid molecules (see for example, Thompson, U.S. Pat. Nos. 5,902,880 and 6,146,886).

In an example, an expression vector can include a nucleic acid sequence encoding at least one siRNA molecule specifically designed to inhibit at least one of the α4, β1 or β7 integrin subunits. In a particular example, the vector contains a sequence(s) encoding both strands of a siRNA molecule comprising a duplex. In another example, the vector also contains sequence(s) encoding a single nucleic acid molecule that is self-complementary and thus forms a siRNA molecule. The recombinant vectors capable of expressing the siRNA molecules can be delivered as described below, and persist in target cells. Alternatively, viral vectors can be used that provide for transient expression of nucleic acid molecules. Such vectors can be repeatedly administered as necessary. Once expressed, the siRNA molecule interacts with the target mRNA and generates an RNAi response.

In additional examples, an agent includes at least two α4β1 or α4β7 antagonists, such as two specific monoclonal antibodies that each bind to their respective integrin subunits and inhibit or reduce HIV. For example, the agent includes a α4 integrin subunit monoclonal antibody and a β7 integrin subunit monoclonal antibody.

Test Agents

The one or more test agents can be any substance, including, but not limited to, a protein (such as an antibody), a nucleic acid molecule (such as a siRNA), an organic compound, an inorganic compound, a small molecule, a peptide or any other molecule of interest. In a particular example, the test agent is an antibody. For example, the antibody is directed to specifically bind to α4 integrin, such as α4β1, α4β7, or αLβ2 integrin. In a particular example, the antibody is directed to the α4, β1, or β7 subunit of the integrin. For example, the antibody is directed to inhibit or reduce the activation of α4 integrin by gp120. In other examples, the test agent is a siRNA that reduces or inhibits the activity (such as the expression) of one of the α4, β1, or β7 subunits.

Administration

Methods of administration of the disclosed agents are routine, and can be determined by a skilled clinician. For example, the disclosed agents (such as those that include an α4β1 or α4β7-specific antagonist for a α4, β1 or β7 integrin subunits) can be administered via injection, orally, topically, transdermally, parenterally, or via inhalation or spray. In a particular example, an α4β1 or α4β7-specific antagonist is administered intravenously to a mammalian subject, such as a human.

The therapeutically effective amount of the agents administered can vary depending upon the desired effects and the subject to be treated. In one example, the method includes daily administration of at least 1 µg of a therapeutic agent to the subject (such as a human subject). For example, a human can be administered at least 1 µg or at least 1000 mg of the agent daily, such as 10 µg to 100 µg daily, 100 µg to 1 mg daily, 100 µg to 1000 mg for example 100 µg daily, 1 mg daily, 10 mg daily, 100 mg daily, or 1000 mg. In an example, the subject is administered at least 1 µg (such as 1-100 µg) intravenously of the therapeutic agent (such as an α4β1 or α4β7-specific antagonist that binds to one of the α4, β1 or β7 integrin subunits). In one example, the subject is administered at least 1 mg intramuscularly (for example in an extremity) of such composition. The dosage can be administered in divided doses (such as 2, 3, or 4 divided doses per day), or in a single dosage daily. In a specific example, the subject is administered at least 0.15 mg per kg of body weight of the agent approximately every four weeks for at least 6 months. For example, 0.15 mg/kg, 0.5 mg/kg, 2 mg/kg, 3 mg/kg, 5 mg/kg or 6 mg/kg is administered, such as via intravenous or subcutaneous injections, every 28 days for 6 months.

In particular examples, the subject is administered the agent that includes an an α4β1 or α4β7-specific antagonist for one of the α4, β1 or β7 integrin subunits on a multiple daily dosing schedule, such as at least two consecutive days, 10 consecutive days, and so forth, for example for a period of weeks, months, or years. In one example, the subject is administered the an α4β1 or α4β7-specific antagonist daily for a period of at least 30 days, such as at least 2 months, at least 4 months, at least 6 months, at least 12 months, at least 24 months, or at least 36 months.

In specific examples, the agent for administration can include a solution of the disclosed an α4β1 or α4β7-specific antagonists dissolved in a pharmaceutically acceptable carrier, such as an aqueous carrier. A variety of aqueous carriers can be used, for example, buffered saline and the like. These solutions are sterile and generally free of undesirable matter. These agents may be sterilized by conventional, well known sterilization techniques. The agents may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody or peptide in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of the disclosed an α4β1 or α4β7-specific antagonists per subject per day. Dosages from 0.1 up to about 100 mg per subject per day may be used. Actual methods for preparing administrable compositions will be known or apparent to those skilled in the art and are described in more detail in such publications as Remington's Pharmaceutical Science, 19th ed., Mack Publishing Company, Easton, Pa. (1995).

The disclosed agents including an α4β1 or α4β7-specific antagonist may be provided in lyophilized form and rehydrated with sterile water before administration, although they are also provided in sterile solutions of known concentration. The agent solution is then added to an infusion bag containing 0.9% Sodium Chloride, USP, and typically administered at a dosage of from 0.5 to 15 mg/kg of body weight. Considerable experience is available in the art in the administration of antibody, peptide, small molecule antagonists, and siRNA drugs. These drugs can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

In some examples, a therapeutically effective amount of a nucleic acid molecule is administered to a subject, such as an siRNA molecule. Nucleic acid molecules, such as siRNA specific for an α4, β1 or β7 integrin subunit, can be administered to cells by a variety of methods known to those of skill in the art, including, but not restricted to, encapsulation in liposomes, by iontophoresis, or by incorporation into other delivery vehicles, such as hydrogels, cyclodextrins, biodegradable nanocapsules, and bioadhesive microspheres, or by proteinaceous vectors (see, for example, O'Hare and Normand, International PCT Publication No. WO 00/53722). Alternatively, the nucleic acid/vehicle combination can be locally delivered by direct injection or by use of an infusion pump. Direct injection of the nucleic acid molecules of the disclosure, whether subcutaneous, intramuscular, or intradermal, can take place using standard needle and syringe methodologies, or by needle-free technologies such as those described by Barry et al., International PCT Publication No. WO 99/31262. Other delivery routes, but are not limited to, oral delivery (such as in tablet or pill form), intrathecal or intraperitoneal delivery. More detailed descriptions of nucleic acid delivery and administration are provided in Sullivan et al., PCT WO 94/02595, Draper et al., PCT WO93/23569, Beigelman et al., PCT WO99/05094 and Klimuk et al., PCT WO99/04819.

The disclosed agents including one or more α4β1 or α4β7-specific antagonists, can further include one or more biologically active or inactive compounds (or both), such as anti-viral agents and conventional non-toxic pharmaceutically acceptable carriers, respectively. Examples of such biologically inactive compounds include, but are not limited to: carriers, thickeners, diluents, buffers, preservatives, and carriers. The pharmaceutically acceptable carriers useful for these formulations are conventional (see Remington's Pharmaceutical Sciences, by E. W. Martin, Mack Publishing Co., Easton, Pa., 19th Edition (1995)). In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can include minor amounts of non-toxic auxiliary substances, such as wetting or emulsifying agents, preservatives, and pH buffering agents and the like, for example sodium acetate or sorbitan monolaurate.

Controlled release parenteral formulations can be made as implants, oily injections, or as particulate systems. For a broad overview of protein delivery systems see, Banga, *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, *Colloidal Drug Delivery Systems*, ed., Marcel Dekker, Inc., New York, N.Y., pp. 219-342 (1994); and Tice & Tabibi, *Treatise on Controlled Drug Delivery*, ed., Marcel Dekker, Inc. New York, N.Y., pp. 315-339, (1992) both of which are incorporated herein by reference.

Polymers can be used for ion-controlled release of the agents disclosed herein. Various degradable and nondegradable polymeric matrices for use in controlled drug delivery are known in the art (Langer, *Accounts Chem. Res.*, 26: 537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.*, 9: 425-434, 1992; and Pec et al., *J. Parent. Sci. Tech.*, 44(2): 58-65, 1990). Alternatively, hydroxyapatite has been used as a microcarrier for controlled release of proteins (Ijntema et al., *Int. J. Pharm.*, 112: 215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

Among various uses of the α4β1 or α4β7-specific antagonists disclosed herein are disease conditions associated with HIV, including HIV infection and HIV replication.

The following examples are provided to illustrate certain particular features and/or embodiments. These examples should not be construed to limit the invention to the particular features or embodiments described.

EXAMPLES

The major envelope protein of HIV-1 is a glycoprotein of approximately 160 kD (gp160). During infection, proteases of the host cell cleave gp160 into gp120 and gp41. gp41 is an integral membrane protein, while gp120 protrudes from the mature virus. Together gp120 and gp41 make up the HIV envelope spike.

The HIV envelope spike mediates binding to receptors and virus entry (Wyatt and Sodroski, *Science*, 280:188, 1998). The spike is trimeric and composed of three gp120 exterior and three gp41 transmembrane envelope glycoproteins. CD4 binding to gp120 in the spike induces conformational changes that allow binding to a coreceptor, either CCR5 or CXCR4, which is required for viral entry (Dalgleish et al., *Nature*, 312:763, 1984; Sattentau and Moore, J. Exp. Med., 174:407, 1991; Feng at al., *Science*, 272:872, 1996; Wu et al., *Nature*, 384:179, 1996; Trkola et al., *Nature*, 384:184, 1996).

The mature gp120 glycoprotein is approximately 470-490 amino acids long depending on the HIV strain of origin. N-linked glycosylation at approximately 20-25 sites makes up nearly half of the mass of the molecule. Sequence analysis shows that the polypeptide is composed of five conserved regions (C1-05) and five regions of high variability (V1-V5).

HIV infection results in the rapid dissemination of virus to gut-associated lymphoid tissue (GALT). Subsequently HIV mediates a massive depletion of gut CD4+ T-cells that contributes significantly to HIV-induced immuno-dysfunction. HIV-1 replicates most efficiently in activated CD4+ T-cells. Large numbers of these cells are found in GALT (Brenchley et al., *Nat. Immunol.*, 7: 235-239, 2006; and Li et al., *Nature*, 434: 1148-1152, 2005). Regardless of the route of transmission, HIV-1 rapidly establishes infection in GALT (Li et al., *Nature*, 434: 1148-1152, 2005; Brenchley et al., *J. Exp. Med.*, 200: 749-759, 2004; Guadalupe et al., *J. Virol.*, 77: 11708-11717, 2003; Mattapallil et al., *Nature*, 434: 1093-1097, 2005; and Veazey et al., *Science*, 280: 427-431, 1998). The migration of leukocytes to specific tissues is mediated by a complex and tightly regulated system of adhesion molecules and integrins (von Andrian and Mackay, *N. Engl. J. Med.*, 343: 1020-1034, 2000).

Homing of lymphocytes to, and retention within GALT is mediated, by α4β7 integrin (Wagner et al., *Nature*, 382: 366-370, 1996). An activated form of α4β7 integrin mediates the transendothelial migration of lymphocytes to the gut through interactions with MadCAM expressed on high endothelial venules in the gut (von Andrian and Mackay, *N. Engl. J. Med.*, 343: 1020-1034, 2000; and Luster et al., *Nat Immunol.*, 6: 1182-1190, 2005). Rhinovirus was the first virus shown to mimic an integrin (Greve et al., *Cell*, 56: 839-847, 1989), and a number of both enveloped and non-enveloped viruses including HHV-8, Hantavirus and papillomavirus all use integrins to facilitate infection (Nemerow and Cheresh, *Nat. Cell Biol.*, 4: E69-E71, 2002). Of note, several strains of type A rotavirus, a major cause of gastroenteritis, interact directly with α4β7 integrin (Graham et al., *J. Gen. Virol.*, 86: 3397-3408, 2005).

Example 1

Materials and Methods for Characterizing HIV-1 gp120 Binding to α4β7 Integrin on NK Cells This example provides the materials and methods utilized for characterizing HIV-1 gp120 binding to α4β7 integrin on NK cells.

Cells and Reagents.

Freshly isolated PBMCs were obtained from healthy donors and separated by Ficoll-Hypaque. Purified CD4+ T cells and NK cells were obtained by negative selection using magnetic beads (StemCell Technologies, Vancouver, BC). Cultured PBMCs were activated with OKT3, IL2 (20 IU/ml) and retinoic acid (RA, 10nM) unless otherwise specified. RA was obtained from Sigma Chemical (St. Louis, Mo.). Recombinant Ig-fusion proteins (MadCAM, VCAM-1, E-cadherin) were purchased from R&D Systems (Minneapolis, Minn.). Integrin antibodies were obtained from Serotech Laboratories Ltd. (Raleigh, N.C.) and Chemicon (Temecula, Calif.), while FITC, PE, APC surface marker antibodies were acquired from Beckton Dickinson (San Diego, Calif.). Cyclic peptides CWLDVC (SEQ ID NO:1) and the scrambled control peptide CDLWC (SEQ ID NO:31) were obtained from NeoMPS (San Diego, Calif.). Recombinant gp120s were produced and purified as described in supplemental methods, using hollow-fiber bioreactors (Fibercell Systems, Frederick, Md.). Integrin cDNA expression vectors were acquired from ORIGENE™ (ORIGENE is a trademark of OriGene Technologies, Inc., Rockville, Md.). Sera from two HIV viremic patients were obtained for binding studies.

Flow Cytometry Binding Assays.

Cells were stained with fluoresceinated mAbs using standard procedures preceded by Fc receptor blocking with human IgG. Buffers used were 10 mM Hepes 150 mM NaCl (HBS Buffer) with 100 µM CaCl, 1 mM MnCl unless otherwise specified. Buffer without divalent cations included 10 mM EDTA. gp120 staining was carried out with biotinylated gp120 (EZ-LINK™ biotinylation reagent Pierce Chemical, Rockville, Ill.; EZ-LINK™ is a trademark of Pierce Chemical) followed by PE conjugated neutravidin/streptavidin (Pierce, Rockville, Ill.). Data were acquired using BD FACSCALIBUR™ (FASCALIBUR is a trademark of Becton Dickinson, San Diego, Calif.).

Transient Transfection of 293T Cells.

293T cells were cotransfected with 2 µg of each integrin expression vector plasmid DNA (total 4 µg) or an empty control vector using POLYFECT™ (POLYFECT is a trademark of Qiagen®, Valencia, Calif.) per the manufacturer's instructions. After 48 hours cells were harvested with versene, rinsed thoroughly and stained as described above.

Tandem Array Mass Spectroscopy.

B7 integrin was identified by tandem array mass spectroscopy. Eluant fractions collected from the gp120 affinity column were resolved by sodium dodecyl sulfate-polyacrylamide gel electrophoresis (SDS-PAGE) on a 4-12% gradient gel. The proteins were visualized by silver staining (Invitrogen, Carlsbad, Calif.). Protein bands were excised individually. The gel bands were destained in 50% acetonitrile in 25 mM $NH_4HCO_3$, pH 8.4 and vacuum dried. A trypsin solution (20 µg/mL in 25 mM $NH_4HCO_3$, pH 8.4) was added to the destained and dried bands. Following incubation on ice for 1 hour, excess trypsin solution was removed and the gel bands were covered with 25 mM $NH_4HCO_3$, pH 8.4. After overnight incubation at 37° C., the tryptic peptides were extracted with 70% acetonitrile, 5% formic acid, lyophilized and desalted using ZIPTIP®s (ZIPTIP® is a registered trademark of Millipore® Corporation, Bedford, Mass.).

Nanoflow reversed-phase liquid chromatography-tandem mass spectrometry (NanoPRLC-MS/MS). The chromatographic separation of the tryptic peptides was conducted using a microcapillary column with an integrated electrospray ionization (ESI) emitter. A 75 µm i.d.×360 µm o.d.×10 cm long fused silica capillary column with a fine flame pulled tip (~5-7 mm orifice) (Polymicro Technologies, Phoenix, Ariz.) was slurry packed in-house with 5 mm, 300 Å pore size C-18 stationary phase (Jupiter, Phenomenex, Torrance, Calif.). The column was connected to an Agilent 1100 nanoflow LC system (Agilent Technologies, Palo Alto, Calif.) and then coupled with a linear ion-trap (LIT) mass spectrometer via a nanoelectrospray source (LTQ, ThermoElectron, San Jose, Calif., operated with Xcalibur 1.4 SR1 software). The capillary temperature and electrospray voltage were set to 160° C. and 1.5 kV, respectively. Mobile phase A was 0.1% formic acid in water and B was 0.1% formic acid in acetonitrile. After the peptide injection, the gradient elution was performed under the following conditions: 2% B at 500 nL/min in 20 min; a linear increase of 2-42% B at 250 nL/min in 40 min; 42-98% B at 250 nL/min in 10 min; 98% B at 500 nL/min for 18 min. The column was then re-equilibrated with 98%-2% B at 500 nL/min for 12 min and washed with 2% B at 500 nL/min for 20 min prior to subsequent sample injection.

The LIT-MS was operated in a data-dependent MS/MS mode where the five most abundant peptide molecular ions in every MS scan were sequentially selected for collision-induced dissociation (CID) using a normalized collision energy of 35%. Dynamic exclusion was applied to minimize redundant MS/MS acquisition of peptides selected previously for CID.

Bioinformatic Analysis. Tandem mass spectra were searched against the UniProt *Homo sapiens* proteomic database from the European Bioinformatics Institute available on the world wide web address of ebi.ac.uk, March 2006 UniProt release, 37542 accession entries) with SEQUEST operating on a 40 node Beowulf cluster (SEQUEST Cluster version 3.1 SR1, Bioworks Browser 3.2). Peptides were searched using fully tryptic cleavage constraints. For a peptide to be considered legitimately identified, it had to achieve a minimal delta correlation ($\Delta C_n$) of 0.08 and stringent charge state-dependent cross correlation ($X_{corr}$) scores of 1.9 for $[M+H]^{1+}$, 2.2 for $[M+2H]^{2+}$, 3.1 for $[M+3H]3+$ peptide molecular ions. From the list of proteins identified, a subset was derived that included only known membrane proteins. This list was then further subdivided into functional categories that included metal-binding proteins using the bioinformatic analysis resource DAVID available on the world wide web address of david.abcc.ncifcrf.gov/home.jsp.

Virion Capture Studies. PBMCs were cultured in OKT3/IL2 and RA as described above. After 6 to 8 days, culture medium was washed away with sterile HBS buffer with or without divalent cations and the cells were resuspended at $1 \times 10^6$ cells/ml in a 96 well plate. Buffer without divalent cations included 10 mM EDTA. Cells were preincubated with human IgG along with blocking agents (anti-CD4 and anti α4 integrin mAbs) where specified. Cells were then incubated with HIV-1 Bal (Applied Biotechnologies Inc., Columbia, Md.) for 30 minutes on ice, rinsed thoroughly, and lysed. Bound virus was measured by p24 Gag antigen capture ELISA (Beckman Coulter, Fullerton, Calif.).

Recombinant Envelope Proteins. All proteins were produced and purified in an identical manner. The mature coding sequences of each envelope protein, from +1 to the gp120-gp41 junction were inserted into a mammalian expression vector downstream of a synthetic leader sequence. Vectors were transfected into either 293T or DHFR-CHO cells (ATCC, Manassas, Va.) using either $CaPO_4$ or POLYFECT™ (Qiagen®, Valencia, Calif.). For stable cell lines, cultures were selected in nucleoside-free media and subjected to increasing concentrations of methotrexate (Sigma, St. Louis, Mo.). Clonal cell lines were established and subsequently seeded into hollow-fiber cartridges (30 kD MW cutoff) (Fibercell systems, Frederick, Md.). Protein containing supernatants were harvested daily from the extracapillary space. Pooled supernatants were passed over a galanthus nivalis lectin column (Vector Labs, Burlingame, Calif.). gp120 was eluted with 500 mM α-methyl-manno pyranoside (Sigma-Aldrich, St. Louis, Mo.), desalted and passed through a cobalt-chelating column to remove contaminants. Protein was then passed over a superdex-200 26/60 gel-filtration column (GE Healthcare Bio-Sciences, Piscataway, N.J.), and peak fractions were collected pooled and concentrated with a stirred cell concentrator (Millipore, Billerica, Mass.). Trace endotoxins were removed from purified protein preparations by triton X114 extraction (Sigma-Aldrich, St. Louis, Mo.), followed by extensive dialysis in HEPES buffered saline pH 7.4. Endotoxin removal was verified by Limulus Amoebocyte Lysate Chromogenic Endpoint Assay (LAL) (Cambrex, East Rutherford, N.J.). Proteins were quantitated by UV adsorption at O.D $\lambda_{280}$ (extinction coefficient 1.1) and values were confirmed by a bicinchoninic acid protein assay (Pierce Chemical, Rockford, Ill.). The recombinant AN1 envelope used to construct a gp120 affinity column was expressed in CHO-lec cells (ATTC, Manassas, Va.). The AN1L182A,D183A variant of AN1 was constructed by inserting a DraIII/MluI fragment in the wild-type AN1 gp120 expression vector with a synthetic fragment (DNA 2.0, Menlo Park, Calif.) that incorporated the L182A and D183A amino acid substitutions. A chimeric SF162P3' was constructed by inserting a synthetic DNA fragment corresponding to nucleotides 98-1286 of SF162P3, which encompasses V1 through V5 domains of the gp120 protein, into the DraIII/MluI si Recombinant Envelope Proteins. The following gp120s were employed in these studies: 93MW959 (GenBank accession # U08453, R5-tropic), 92TH14-12 (GenBank accession #U08801, R5-tropic), 93Ug037 (GenBank accession # U51190, R5-tropic), AN1 gp120 (sequence available at website with a web address of ubik.mullins.microbiol.washington.edu/HIV/Doria-Rose2005/, R5-tropic), and 92Ug21-9 (GenBank accession # U08804, X4-tropic). Two gp120s, P.13-53 (GenBank accession # AF138157), and P.13-59 (GenBank accession # AF138158), were cloned from a chronically infected patient as described in Shankarappa et al. (J. Virol., 73: 10489-10502, 1999). All proteins were produced and purified in an identical manner. The mature coding sequences of each envelope protein, from +1 to the gp120-gp41 junction were inserted into a mammalian expression vector downstream of a synthetic leader sequence. Vectors were transfected into DHFR-CHO cells (ATCC, Manassas, Va.) using either CaPO$_4$ or POLYFECT™ (Qiagen®, Valencia, Calif.). Cells were selected in nucleoside-free media and subjected to increasing concentrations of methotrexate (Sigma-Aldrich, St. Louis, Mo.). Clonal cell lines were established and subsequently seeded into hollow-fiber cartridges (30 kD MW cutoff; Fibercell Systems, Frederick, Md.). Protein containing supernatants were harvested daily from the extra-capillary space. Pooled supernatants were passed over a galanthus nivalis lectin column (Vector Labs, Burlingame, Calif.). gp120 was eluted with 500 mM α-mannose pyranoside (Sigma St. Louis, Mo.), desalted and passed through a cobalt-chelating column to remove contaminants. Protein was then passed over a supedex-200 26/60 gel-filtration column (GE Healthcare Bio-Sciences, Piscataway, N.J.), and peak fractions were collected pooled and concentrated with a stirred cell concentrator (Millipore®, Billerica, Mass.). Trace endotoxins were removed from purified protein preparations by triton X114 extraction (Sigma Chemical Co., St. Louis, Mo.; Sattentau et al., J. Exp. Med. 170: 1319-34, 1989), followed by extensive dialysis in HEPES buffered saline pH 7.4. Proteins were quantitated by UV adsorption at O.D $\lambda_{280}$ (extinction coefficient 1.1) and values were confirmed by a bicinchoninic acid protein assay (Pierce, Rockford, Ill.). The recombinant AN1 envelope used to construct a gp120 affinity column was expressed in CHO-lec cells (ATTC). The AN1L182A,D183A variant of AN1 was constructed by replacing a DraIII/MluI fragment in the wild-type AN1 gp120 expression vector with a synthetic fragment (DNA 2.0, Menlo Park, Calif.) that incorporated the L182A and D183A amino acid substitutions.

Surface Plasmon Resonance Spectroscopy. AN1 or AN1L182A, D183A gp120 were immobilized to separate flow cells of a Biacore 3000 optical biosensor using amine coupling chemistry (Biacore, Inc., Piscataway, N.J.) to a surface density of approximately 500RU each. Alcohol dehydrogenase was immobilized to a similar density in a separate flow cell to control for non-specific interactions. Increasing concentrations of sCD4 (D1D2) or mAbs were passed sequentially over the immobilized proteins in running buffer (10 mM HEPES, pH 7.4, 150 mM NaCl, 3 mM EDTA, 0.01% Tween-20, 0.1% soluble carboxymethyl dextran) at a flow rate of 25 μL/min for 2 min at 25° C., followed by a dissociation phase of 1 or 2 min. The data were analyzed using BiaEvaluation 4.1 Software (Biacore AB, Uppsala, Sweden) using a 1:1 (Langmuir) binding model.

Recombinant gp120 Protein Labeling. Purified recombinant gp120s were biotinylated using amine-coupling chemistry. Proteins were reacted with a 20-fold molar excess of EZ-LINK™ NHS-Biotin (Pierce Chemical, Rockford, Ill.) for 30 min, and reactions were quenched by rapid buffer-exchange into HBS. Biotin incorporation was determined by reacting gp120s with 4'-hydroxyazobenzene-2-carboxylic acid-avidin conjugates (HABA) per the manufacturer's instructions (Pierce Chemical, Rockford, Ill.). Matched protein preparations exhibiting a 1.0-1.2 mol/mole, biotin/gp120 incorporation were used in comparative semi-quantitative flow-cytometric binding assays.

Bioinformatic Analysis. Tandem mass spectra were searched against the UniProt Homo sapiens proteomic database from the European Bioinformatics Institute (world wide web address ebi.ac.uk/, March 2006 UniProt release, 37542 accession entries) with SEQUEST operating on a 40 node Beowulf cluster (SEQUEST Cluster version 3.1 SR1, Bioworks Browser 3.2). Peptides were searched using fully tryptic cleavage constraints. For a peptide to be considered legitimately identified, it had to achieve a minimal delta correlation ($\Delta C_n$) of 0.08 and stringent charge state-dependent cross correlation ($X_{corr}$) scores of 1.9 for $[M+H]^{1+}$, 2.2 for $[M+2H]^{2+}$, 3.1 for [M+3H]3+ peptide molecular ions. From the list of proteins identified, a subset was derived that included only known membrane proteins. This list was then further subdivided into functional categories that included metal-binding proteins using the bioinformatic analysis resource DAVID (web address of david.abcc.ncifcrf.gov/home.jsp).

Flow Cytometry Binding Assays. Cells were stained with fluoresceinated mAbs using standard procedures preceded by Fc receptor blocking with human IgG. Buffers used were 10 mM Hepes 150 mM NaCl (HBS Buffer) with 100 μM CaCl$_2$, 1 mM MnCl$_2$ unless otherwise specified. Buffer without divalent cations included 10 mM EDTA. gp120 staining was carried out with biotinylated gp120 (EZ-LINK™ biotinylation reagent Pierce Chemical, Rockville Ill.) followed by PE conjugated neutravidin/streptavidin (Pierce Chemical, Rockville Ill.). Data were acquired using a BD FACSCalibur.

Transient Transfection of 293T Cells. 293T cells were co-transfected with 2 µg of each integrin expression vector plasmid DNA (total 4 µg) or an empty control vector using POLYFECT™ (Qiagen®, Valencia, Calif.) per the manufacturer's instructions. After 48 hours, cells were harvested with versene, rinsed thoroughly and stained as described above.

p38 Phosphorylation. Natural Killer (NK) cells were obtained by negative selection using magnetic beads (StemCell Technologies, Vancouver, BC) were cultured in RPMI containing 10% FBS+200 U/ml IL2+10nM RA. Cells were treated with 50 nM gp120 or PHA (2 µg/ml) for 5 minutes at 37° C. Cells were immediately pelleted and lysed with Phospho-Safe extraction reagent (Novagen, San Diego, Calif.) followed by denaturation buffer (Flex Set, BD Biosciences San Jose Calif.). Lysates (10 µg) were reacted with phosph-p38 mAb conjugated fluoresceine beads according to the manufacturer's instructions, and analyzed on a BD FACS-array. The reactions were placed on ice and incubated with either PE conjugated MEM-148 or biotin-ICAM-1-Ig, without removal of the envelope protein. Cells were rinsed twice with staining buffer. For biotinylated ICAM-1-Ig, a second streptavidin PE incubation step was added, followed by additional rinses. Analysis by flow cytometry was carried out as described above.

LFA-1 Activation Assays. Highly purified (>95%) CD4+ T-cells were cultured in RA/IL2 for a minimum of 12 days prior to use. Unless specified, IL2 and RA were removed ~18 hrs. prior to the start of each assay. Cells were treated with 50 nM gp120 for 10 minutes at 37° C. in HBS/100 nM $Ca^{++}/1$ mM $Mn^{++}/0.5\%$ BSA, then place on ice and incubated with either PE conjugated MEM-148 or biotin-Icam-1-ig, without removal of the envelope protein. Cells were rinsed 2× with staining buffer. For biotinylated ICAM-1-Ig, a second streptavidin PE incubation step was added, followed by additional rinses. Analysis by flow cytometry was carried out as described above.

Single-Round HIV Infection Assay. HIV infection of $CD4^+$ T cells was quantified by a previously published real-time PCR based assay (Chun et al., *Proc. Natl. Acad. Sci. U.S.A.* 100: 1908-13, 2003). Briefly, ICAM-1 bearing HIV Bal was produced by transient transfection of 293T cells as previously described Tardif & Tremblay (*J. Virol.,* 79: 13714-13724, 2005). Highly purified $CD4^+$ T cells were cultured in media containing RA for at least 10 days prior to infection. Approximately 18 hrs prior to infection cells were placed in media without IL2 unless specified. Cells ($2 \times 10^6$) were inoculated with virus plus or minus simultaneous addition of HP2/1 or IgG1 (2.5 µg) in a total volume of 1 ml and incubated at 37° C. for 4 hrs. Following incubation, cells were rinsed extensively and lysed. Genomic DNA was isolated with a Puregene DNA isolation kit according to the manufacturer's specifications (Qiagen®, Valencia, Calif.). One microgram of DNA was then used as template for real-time PCR in a 7900HT cycler (Applied Biosystems, Foster City, Calif.). Amplification reactions were carried out in triplicate using 0.5 µM primers, 0.2 µM fluorescent probe, and the TAQMAN® (TAQMAN is a registered trademark of Roche Molecular Systems, Inc., Pleasanton, Calif.) gene expression master mix (Applied Biosystems, Foster City, Calif.) in 50 µl total volume. The following primers and probe were used: 5'-GGTCTCTCTGGTTAGACCAGAT-3' (5' primer; SEQ ID NO:2) and 5'-CTGCTAGAGATTTTC-CACACTG-3' (3' primer; SEQ ID NO:3), along with the fluorescent probe 5'-6FAM-AGTAGTGTGTGCCCGTCT-GTT-TAMRA-3' (SEQ ID NO:4). PCR conditions included a denaturation step at 95° C. for 3 minutes followed by 45 cycles of 15 sec at 95° C. and 1 min at 58° C. Serially diluted ACH-2 DNA was also subjected to the above PCR to obtain standard curves. Significance of inhibition (p value) by HP2/1 relative to IgG1 was calculated with a two-tailed Student's T test.

Example 2 gp120 Binding to Primary NK Cells is Mediated by Integrin α4β7

This example illustrates that gp120 binding to primary NK cells is mediated via integrin α4β7.

The mechanism of gp120 for disrupting cytolytic activity was investigated by determining that a panel of genetically diverse recombinant envelope proteins (subgroups A, B, and C) bind NKs in the presence of $Ca^{++}$ (FIG. 1*a*). This data indicated that gp120 was binding to a C-type lectin receptor, yet none of the known gp120 specific C-type lectins is expressed on these cells. To identify the receptor(s) that mediates gp120 binding to NKs, a lysate derived from $10^9$ uncultured NKs was passed over a gp120 affinity column in the presence of $Ca^{++}$. Bound proteins were eluted with EDTA, electrophoresed and identified by tandem mass spectroscopy. No C-type lectin receptors were eluted, however β7 integrin was among the receptors identified. On NKs β7 integrin pairs with α4 integrin (CD49d). The activity of this heterodimer is regulated in part by divalent cations, such that binding to its natural ligands is enhanced when $Ca^{++}$ is replaced by either $Mg^{++}$ or $Mn^{++}$ (Day et al., *Cell Commun. Adhes.,* 9: 205-219, 2002). NKs were stained with the same panel of gp120s in the presence of $Mn^{++}$, and observed enhanced binding for each of the four gp120s employed (FIG. 1*b*). Subsequently, NKs were stained with gp120 in the presence or absence of a recombinant MadCAM-Ig, an addressin specific for α4β7 integrin, and found that it efficiently competed gp120 binding, while a control Ig fusion protein, NKG2D-Ig, did not (FIG. 1*c*). This data indicated that gp120 was binding to α4β7 integrin on NK cells. To demonstrate this, 293T cells were co-transfected with α4 and β7 integrin expression vectors. Both receptors were highly expressed as evidenced by reactivity with α4 and β7 integrin monoclonal antibodies (mAbs) (FIG. 1*d*). gp120 bound significantly more to α4β7 integrin co-transfected cells than to mock transfected cells, and this reactivity was blocked by unlabeled MadCAM-Ig (FIG. 1*e*). Because the principal MadCAM-1 contact sites on α4β7 integrin reside in α4 integrin subunit, the ability of gp120 to bind to α4β1 integrin was also investigated. Overexpression of α4β1 integrin on 293T cells resulted in a minor increase in gp120 binding. These data indicate that gp120 binds to an activated form of α4β7 integrin.

Example 3

Activated α4β7 Integrin on CD4+ and CD8+ T-Cells Recognize HIV gp120

Figure 3A:
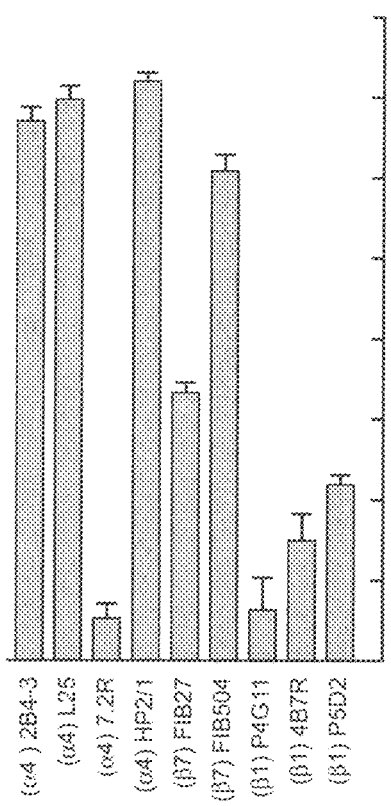
FIGS. 3a-3d illustrate that CD4 independent binding of gp120 on retinoic acid (RA)-treated T-cells is mediated by α4β7 integrin.
Figure 3B:
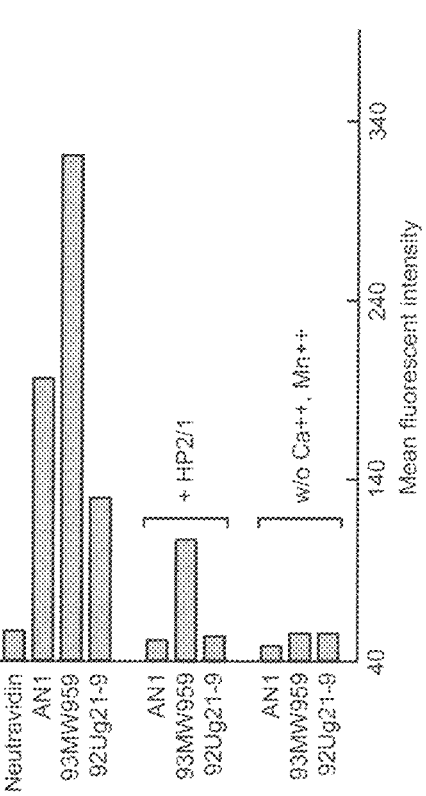
Figure 3C:
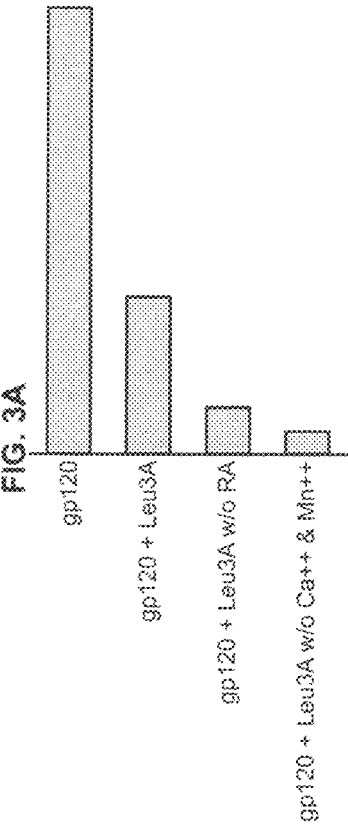
Figure 3D:
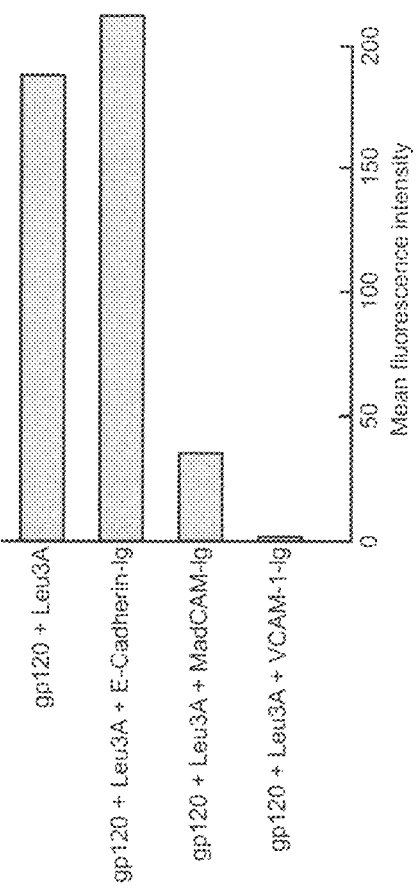
Figure 4A:
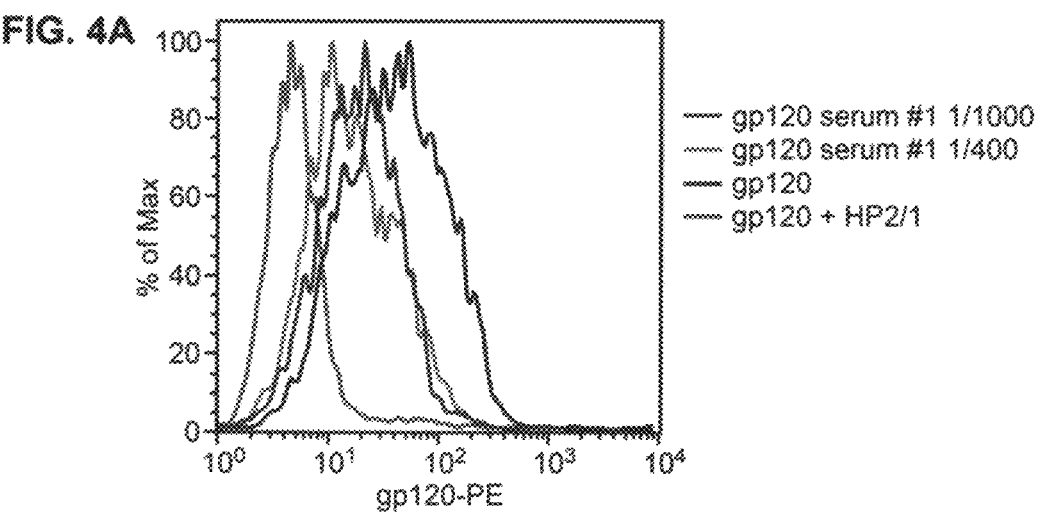
FIGS. 4a and 4b illustrate inhibition of gp120 binding to RA-treated CD8+ T-cells by HIV+ immune sera. RA-treated CD8 T-cells stained with biotinylated AN1 gp120 in the absence or presence of serum from two HIV+ individuals at different dilution, or the α4 integrin mAb HP2/1.
Figure 4B:
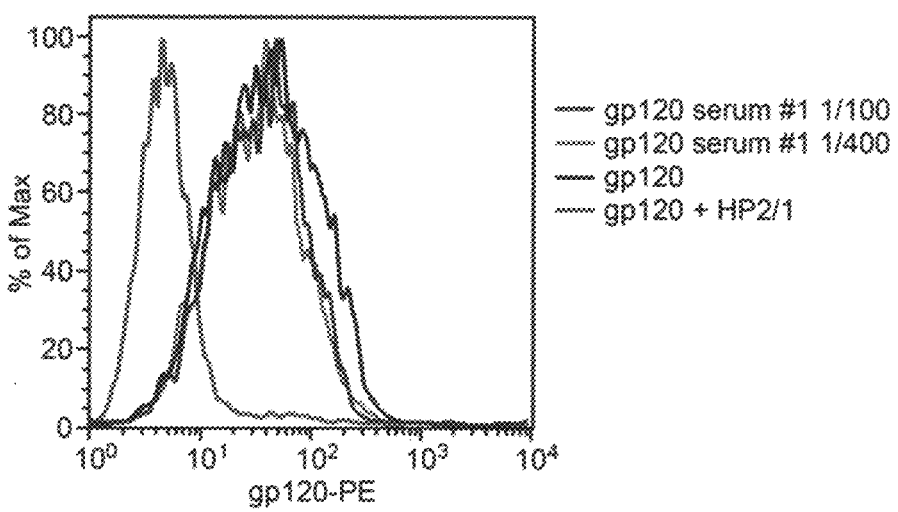
Figure 6A:
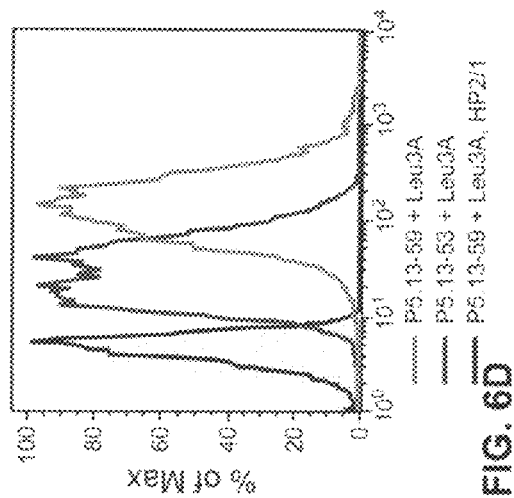
FIGS. 6a-6d illustrate variation in α4β7 integrin binding activity among gp120s.
Figure 6B:
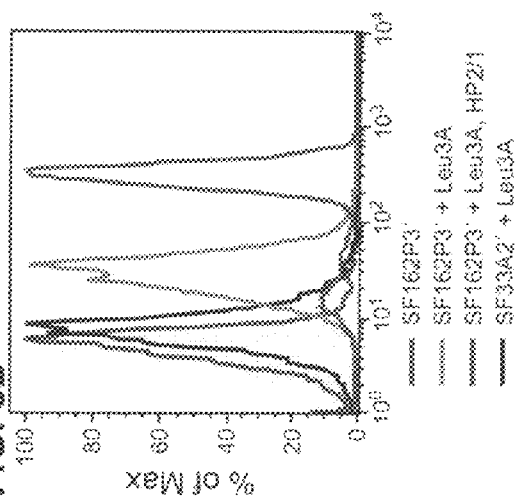
Figure 6C:
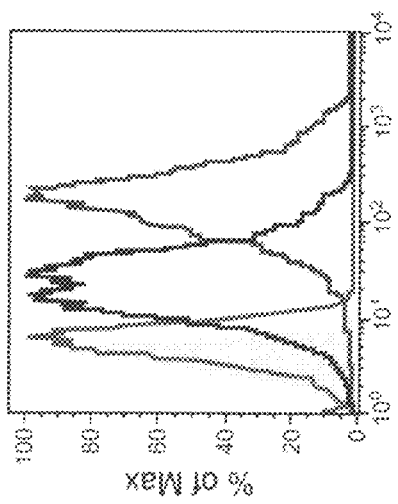
Figure 6D:
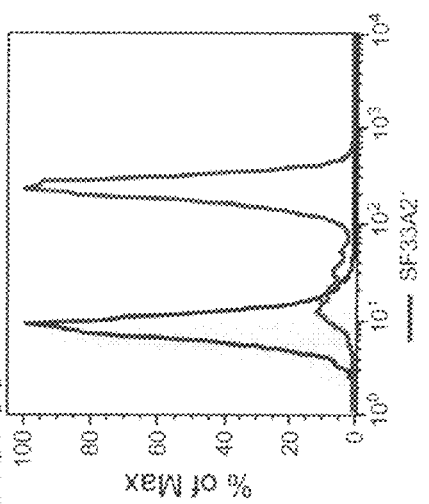
Figure 7A:
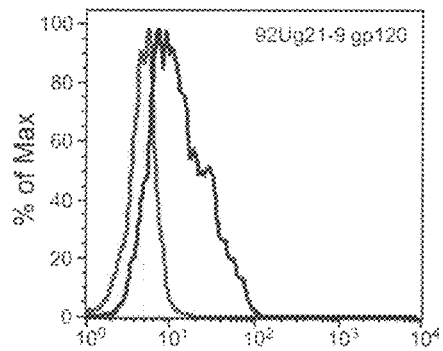
FIGS. 7a-7e illustrate gp120 binding to integrin α4 and α4β1.
Figure 7B:
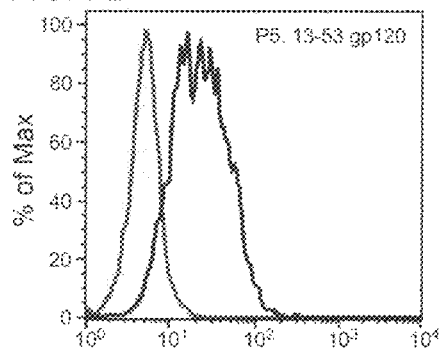
Figure 7C:
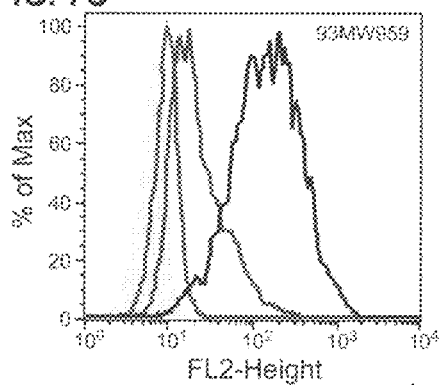
Figure 7D:
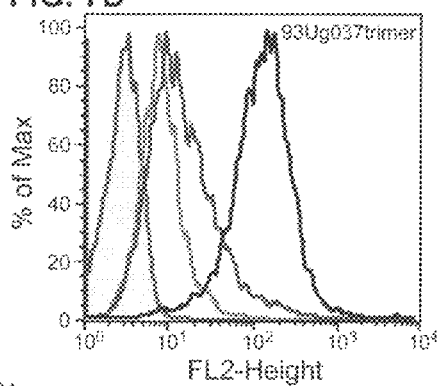
Figure 7E:
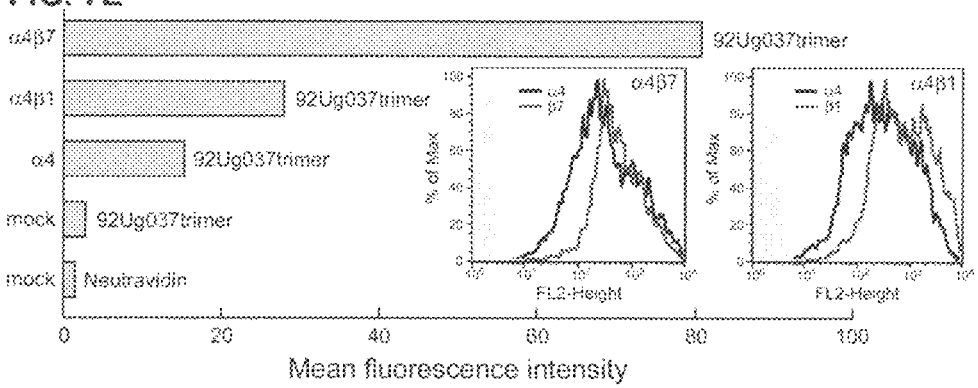

This example illustrates that HIV gp120 is recognized by α4β7 integrin on CD4+ and CD8+ T-cells.

α4β7 integrin is the principal integrin involved in lymphocyte homing to the lamina propria of GALT (von Andrian et al., *N. Eng. J. Med.,* 343: 1020-1034, 2000). Of note, the primary targets of HIV replication are CD4+ T-cells localized to lymphoid tissues, and for CCR5 utilizing isolates, GALT is the predominant site of replication particularly GALT (Brenchley et al., *Nat. Immunol.*, 7:235-239, 2006). Additionally, viral replication in GALT early in infection is coupled with a dramatic depletion of CD4+ T-cells, that is thought to contribute substantially to HIV associated immuno-dysfunction (Picker, *Curr. Opin. Immunol.*, 18: 399-405, 2006). The ability of gp120 to bind to α4β7 integrin on T-cells was determined. Although circulating T-cells express both α4 and β7 integrin subunits the vast majority of heterodimers are present in an inactive conformation. Specialized dendritic cells in mesenteric lymph nodes and Peyers patches convert vitamin A to RA, which acts directly on T-cells to imprint a gut-homing phenotype, that includes inducing an active conformation of α4β7 integrin (Iwata et al., *Immunity*, 21: 527-538, 2004). A GALT-like phenotype, in which both CD4+ and CD8+ T-cells express high levels of active α4β7 integrin, can be induced by culturing peripheral blood mononuclear cells (PBMCs) in the presence of RA (Iwata et al., *Immunity*, 21: 527-538, 2004). PBMCs were cultured in the presence of RA and observed increased expression of α4 and β7 integrin subunits (FIG. 2). To measure CD4-independent binding on CD4+ T-cells, CD8 depleted PBMCs were stained with labeled gp120 in the presence of unlabeled Leu3A, an anti-CD4 receptor mAb that inhibits gp120 binding (Sattentau et al., *J. Exp. Med.*, 170: 1319-1334, 1989). Substantial CD4-independent binding was observed as indicated by residual binding in the presence of Leu3A (FIG. 3a). This binding was abrogated when divalent cations were excluded (FIG. 3a). Little CD4-independent binding was observed in cells cultured in the absence of RA (FIG. 3a). CD4-independent gp120 binding was inhibited by both MadCAM-Ig and VCAM-Ig, but not by the closely related E-cadherin-Ig, which is specific for α4β7 integrin (FIG. 3b). The principal contact sites for the natural ligands of α4β7 integrin reside on the α chain (Zeller et al., *J. Cell Biochem.*, 83: 304-319, 2001). Three α4 integrin subunit mAbs, HP2/1, L25, and 2B4-3 also inhibited gp120 binding to α4β7 integrin (FIG. 3c). These mAbs map to sites between residues 152-203 of α4 integrin, and recognize epitopes close to the Madcam and VCAM binding sites (Schiffer et al., *J. Biol. Chem.*, 270: 14270-14273, 1995). The two β7 mAbs tested, FIB504 and FIB27, partially inhibited gp120 binding (FIG. 3c), while three β1 mAbs had a minimal effect. These results demonstrate that gp120 binds to α4β7 integrin on CD4+ T-cells, at a site(s) close to the epitopes recognized by its natural ligands. Binding to CD8+ T-cells was also assayed. gp120 bound to CD8+ T-cells in a manner that was inhibitable by the α4 integrin mAb HP2/1, and was dependent on divalent cations (FIG. 3d). Immune-sera from HIV infected patients was also determined to inhibit binding of gp120 to α4β7 integrin on CD8+ T-cells (FIG. 4). gp120 appears on virions as trimeric spikes. In this regard, it was determined that both recombinant gp120 trimers and whole virions also bound α4β7 integrin (FIG. 5).

Although gp120s from subtypes A, B, C and D all bound α4β7 integrin, distinct differences in reactivities were observed (FIGS. 1a, 1b, and 2d). Upon further investigation differences in α4β7 integrin binding activity are evident, even when comparing closely related gp120s derived from a single patient (FIG. 6).

The principal MadCAM and VCAM contact sites on α4β7 integrin reside is α4 integrin subunit. It was determined that for those monomeric envelope proteins that exhibited the strongest α4β7 integrin binding activity, low level binding could be detected both to α4 integrin alone and to α4β1 integrin (FIG. 7).

Example 4

α4β7 Integrin Binding-Site on gp120 Resides in the V2-Loop

This example illustrates that a α4β7 integrin binding-site on gp120 resides in the V2-loop.

Figure 8A:
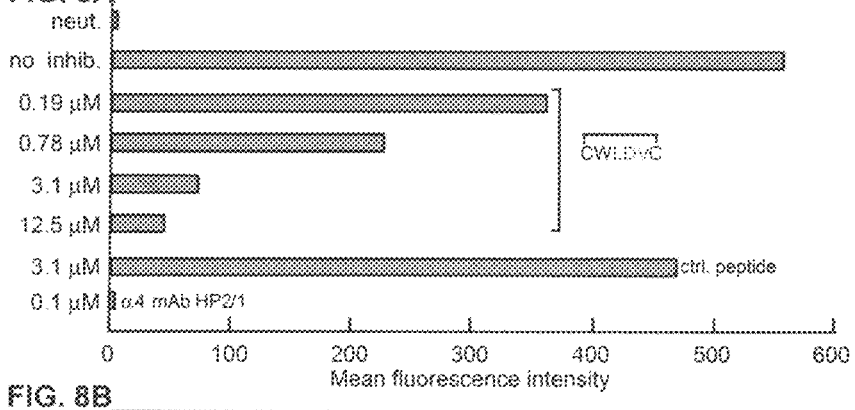
FIGS. 8a-8c illustrate that binding of gp120 to α4β7 integrin involves an LDV sequence in the gp120 V2 loop.
Figure 8B:
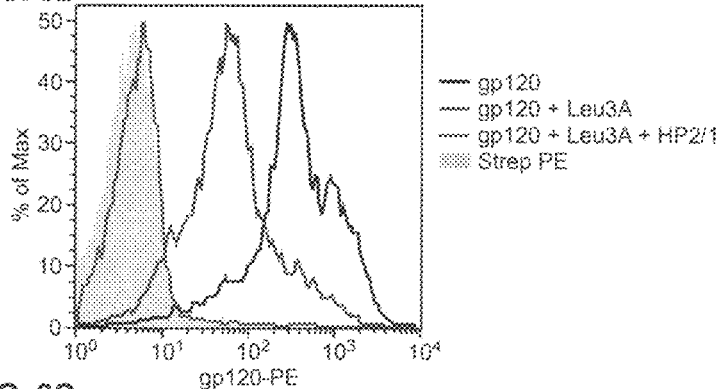
Figure 8C:
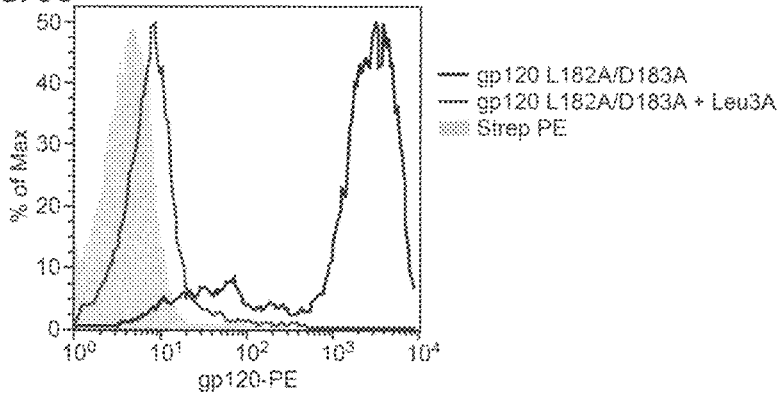
Figure 10:
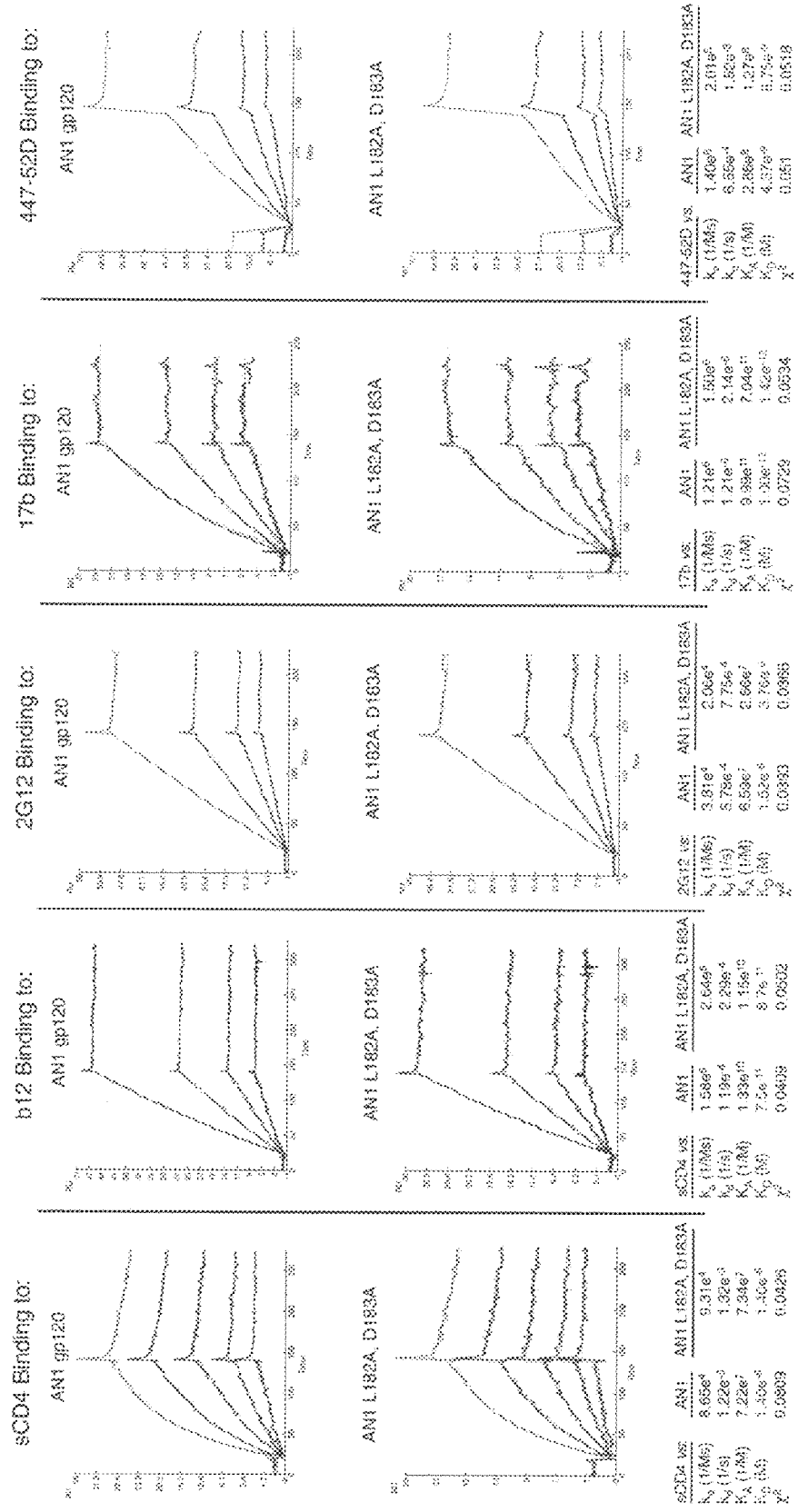
FIG. 10 provides a series of binding kinetic profiles comparing sCD4 and HIV1 gp120 mAbs binding to AN1 gp120 or An1L182A,D183A. Kinetics of sCD4 (D1D2), and 4 mAbs (b12, 2G12, 17b, and 447-52D) binding to AN1 gp120 or AN1L182A,D183A as measured by surface plasmon resonance sp

MadCAM, VCAM and fibronectin all bind α4β7 integrin through structurally homologous binding motifs (Jackson, *Curr. Pharm. Des.*, 8: 1229-1253, 2002). For MadCAM, the minimal essential epitope is a short tripeptide loop, LDT, while in fibronectin the sequence is LDV, and in VCAM the sequence is IDS. In each case the core aspartic acid residue plays a pivotal role, and its removal abrogates binding (Jackson, *Curr. Pharm. Des.*, 8: 1229-1253, 2002). It was determined if a cyclic hexapeptide CWLDVC (SEQ ID NO: 1; cyclic in the C) containing the core LDV loop, which has been shown to inhibit binding of all three natural ligands to α4β7 integrin (Vanderslice et al., *J. Immunol.* 158: 1710-1718, 1997), would also inhibit gp120 binding to α4β7. gp120-binding to RA cultured CD8+ T-cells was inhibited by CWLDVC in a dose dependent manner (FIG. 8a). This suggests that HIV might recognize α4β7 integrin by mimicking the tripeptide loop present in its natural ligands. Indeed, polyoma virus VP1 employs an LDV sequence to bind α4β1 (Caruso et al., *J. Mol. Biol.*, 367: 54-64, 2007). Inspection of the HIV envelope sequence reveals a single consensus LDV in the V2 loop, at position 182-184 (HXB2 numbering) (FIG. 9). The D at position 183 is conserved in >98% of the 976 gp120 sequences in the 2006 HIV sequence data-base of aligned envelope sequences. A mutant form of AN1 gp120 was constructed and expressed in which L182 and D183 were replaced with alanines. Using surface plasmon resonance assays, mutant gp120 was determined to recognize sCD4 and several conformationally sensitive gp120 mAbs, including the V2-loop mAb 697-30D, with binding kinetics similar to the w.t. AN1 gp120, indicating that the mutant protein was conformationally intact (FIG. 10). In cell surface staining assays, the mutant AN1 gp120 bound CD4 to a greater extent than its w.t. parent (FIGS. 8b and 8c). However, unlike the w.t. AN1 gp120, the mutant envelope exhibited only minor CD4-independent binding to PBMCs (FIGS. 8b and 8c). These studies suggest that HIV-1, like polyoma virus, presents a structure on its envelope that mimics the tripeptide loop present in each of the natural ligands of α4β7, and this tripeptide in large measure, mediates α4β7 integrin binding. Interestingly, subtype C gp120s typically encode an LDI loop in place of LDV.

Example 5 gp120 Transduces Signals Through α4β7 Integrin

This example illustrates that gp120 transduces signals through α4β7 integrin.

Figure 11:
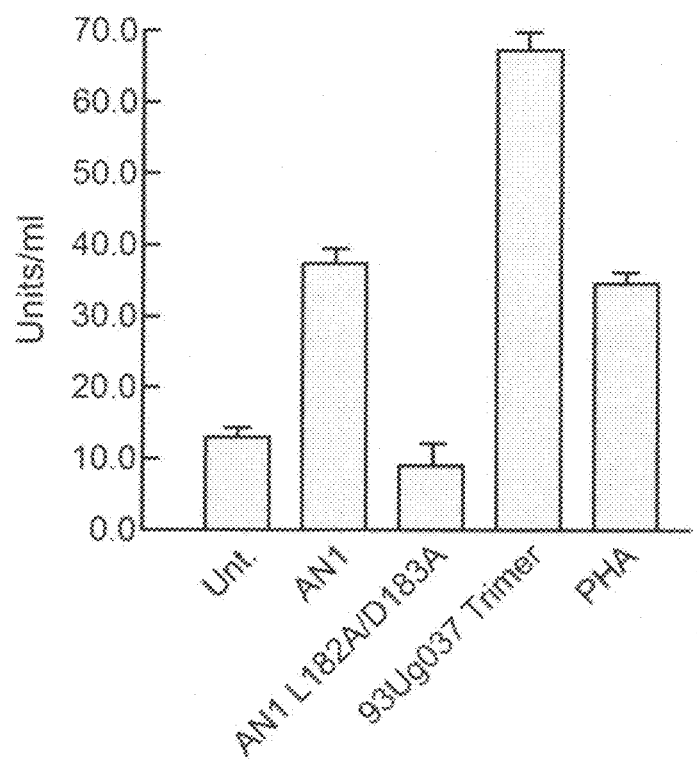

Both enveloped and non-enveloped viruses utilize integrins to facilitate infection (Nemerow et al., *Nat. Cell Biol.*, 4: E69-E71, 2002; and Akula et al., *Cell*, 108: 407-419, 2002). It was determined if gp120 could deliver signals through α4β7 integrin. NK cells were utilized because freshly isolated NK cells, unlike other lymphocyte subsets, present a significant fraction α4β7 integrin heterodimers in a partially activated form. In addition, virtually all gp120 binding to fresh NK cells (which do not express CD4) is mediated by α4β7 integrin (FIG. 1c). The biological activity of the w.t. AN1 gp120 was compared to L182A/D183A AN1 gp120. The mitogen activated protein kinase p38 is rapidly phosphorylated upon engagement of integrins (Bryceson et al., *Immunol. Rev.*, 214: 73-91, 2006). NK cells were treated with either w.t. or the mutant AN1 gp120, and then reacted cell lysates with phospho-specific p38 mAb conjugated fluorescent beads. Significant levels of p38 phosphorylation were observed in cells treated with the w.t gp120, but not with the non-α4β7 integrin-binding mutant gp120 (FIG. 11; see, for example, 5 minutes post-treatment). NK cells were also treated with a trimeric envelope protein, and even higher levels of p38 phosphorylation were observed. Thus, gp120 can transduce intracellular signals through α4β7 integrin.

Example 6 gp120 Ligation of α4β7 Integrin Rapidly Induces the Activation of LFA-1 on Suboptimally Activated CD4+ T-Cells This example illustrates that gp120 ligation of α4β7 integrin rapidly induces activation of LFA-1 on suboptimally activated CD4+T-cells.

Figures 12A, 12B, 12C, 12D, 12E, 12F:
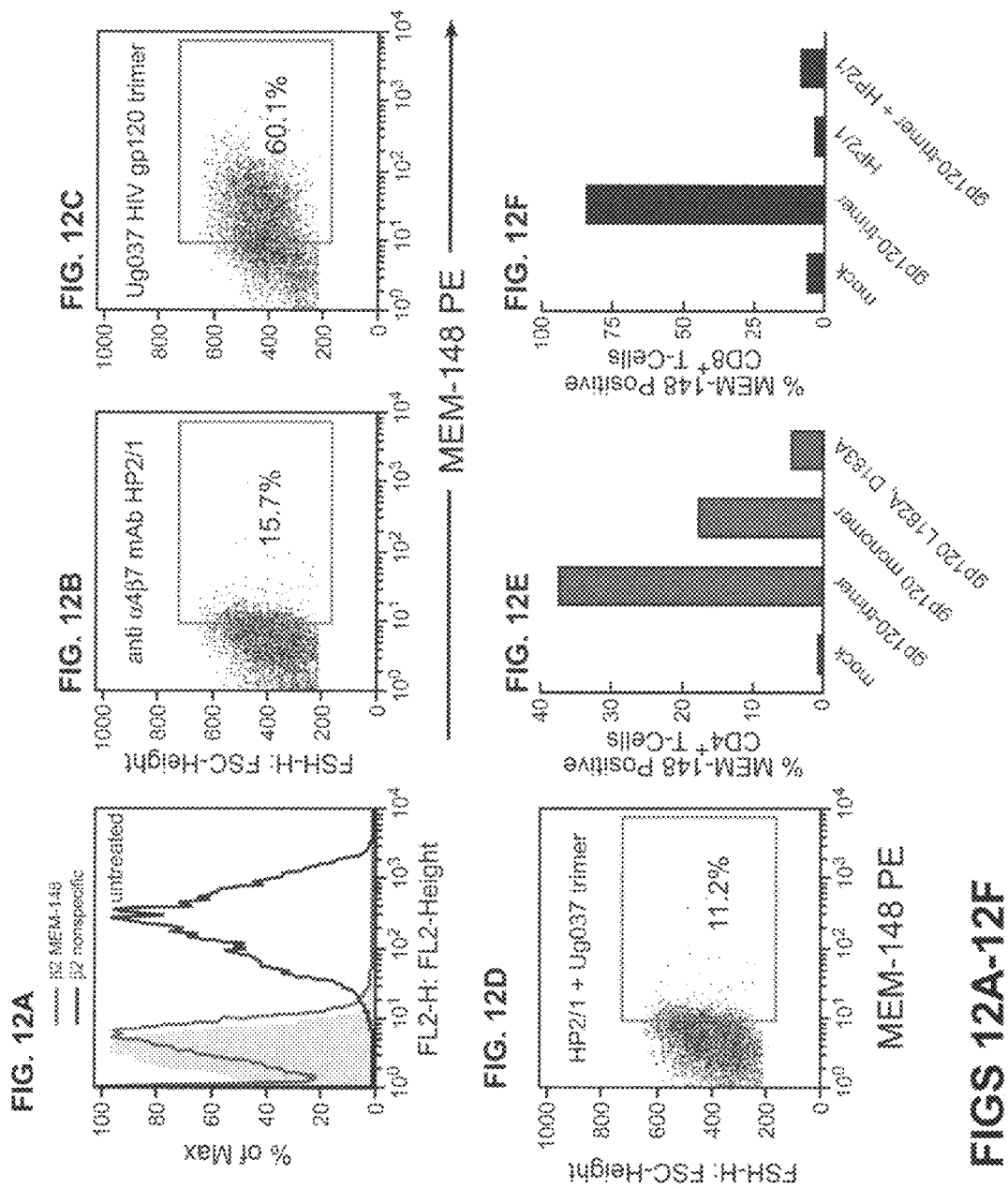
Figures 13A, 13B, 13C, 13D:
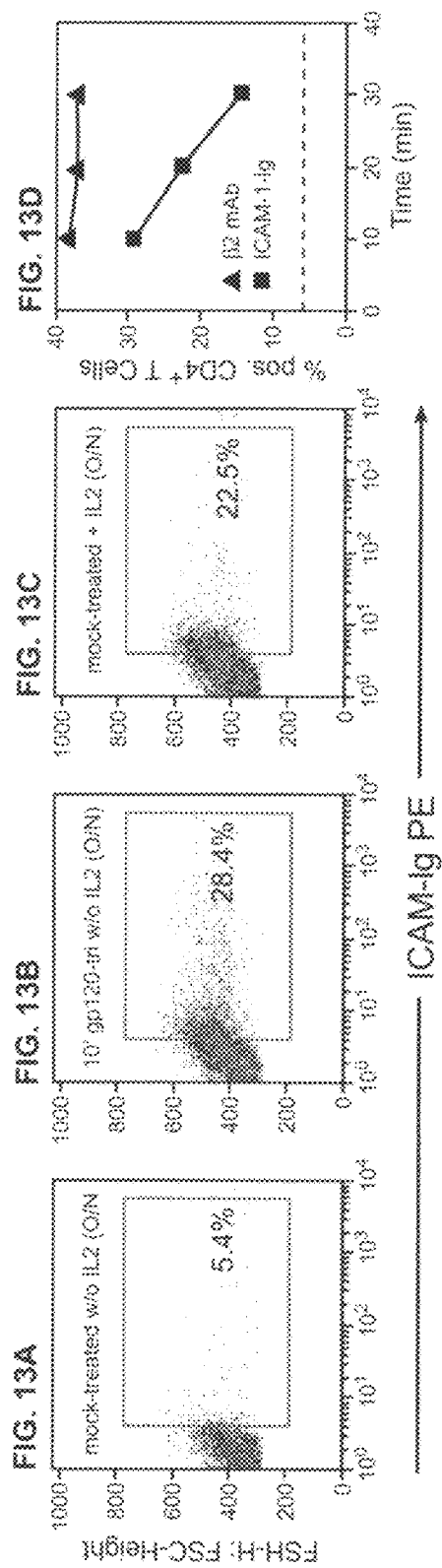

The biological activity of gp120-α4β7 integrin interactions on CD4+ T-cells was determined. In addition to α4β7 integrin, a second integrin, LFA-1 (αLβ2) facilitates homing of T-cells to the gut (Bargatze et al., *Immunity*, 3: 99-108, 1995). Like α4β7 integrin, LFA-1 exists in several conformations that exhibits variable affinities for its natural ligands, which include ICAM-1. Of note, α4β7 integrin on CD4+ T-cells, directly modulates LFA-1 conformation such that MadCAM ligation to α4β7 integrin rapidly induces a change in LFA-1 conformation from a low-affinity state to a higher-affinity state (Bargatze et al., *Immunity,* 3: 99-108, 1995). The coupling of α4β7 integrin with LFA-1 normally occurs only in the gut. Whether gp120 could activate LFA-1 was investigated. Such an activity would be of interest insofar as activated LFA-1 renders CD4+ T-cells more susceptible to HIV infection (Fortin et al., *J. Virol.,* 72: 2105-2112, 1998). Two related mechanisms explain this increased susceptibility. LFA-1 interactions with ICAM-1 play a central role in the establishment of virological synapses (Piguet and Sattentau, *J. Clin. Invest.,* 114: 605-610, 2004) which facilitates efficient cell-to-cell spread of HIV (Jolly et al., *J. Exp. Med.,* 199: 283-293, 2004). In addition, LFA-1 on CD4+ T-cells, by engaging ICAM-1 on cell free virions increases the efficiency of infection (Tardif et al., *J. Virol.,* 79: 13714-13724, 2005). Importantly, only intermediate/active conformations of LFA-1 promotes HIV infection (Fortin et al., *J. Virol.,* 72: 2105-2112, 1998). Thus, gp120-mediated activation of LFA-1 could provide a mechanism to increase the efficiency of infection. To measure LFA-1 activation the integrin β2 (β2) mAb, MEM-148 (Drbal et al., *Immunobiology,* 203: 687-698, 2001), was employed. This mAb only recognizes active forms of LFA-1, and once bound, locks the active conformation in place. RA treated CD4+ T-cells were cultured overnight in the absence of IL2 to reduce basal LFA-1 activation. These suboptimally activated cells readily bound a non-specific β2 mAb, that recognizes both low- and high-affinity conforms of β2. In contrast, little MEM-148 activity was evident (FIG. 12a), indicating that the majority of the LFA-1 was in a low-affinity conformation. When the same cells were treated with HP2/1, a α4β7 integrin mAb that blocks gp120 binding, MEM-148 reactivity was unchanged (FIG. 12b). Cells treated for 10 minutes with a trimeric gp120 showed a marked increase in MEM-148 reactivity (FIG. 12c), while cells treated with the same gp120-trimer in the presence of HP2/1 showed no increase in MEM-148 reactivity (FIG. 12d). Thus, trimeric gp120 induces the activation of LFA-1, in a manner that is inhibitable by a α4β7 integrin mAb that blocks gp120-binding. The w.t. was compared with a V2-loop mutated versions of AN1 gp120. In comparison to the trimeric gp120, w.t. AN1 gp120, which is a monomer, induced MEM-148 reactivity to a lesser degree, but well above background (FIG. 12e). In contrast, the V2-loop mutated AN1 gp120, which binds poorly to α4β7 integrin, induced only a minor increase in MEM-148 reactivity (FIG. 12e). Also, a gp120-trimer induced MEM-148 reactivity on RA-cultured CD8+ T-cells in a manner that is inhibitable by HP2/1 (FIG. 5f). The capacity of gp120 to induce ICAM-1 binding directly was determined by employing labeled ICAM-1-Ig. Unlike MEM-148, ICAM-1-Ig does not lock-in the active conformation of LFA-1. Mock-treated CD4+ T-cells showed little ICAM-1-Ig binding, however a 10 minute treatment with trimeric gp20 resulted in increased ICAM-1-Ig reactivity (FIGS. 13a and 13b). When cells were incubated with the gp120 trimer for longer periods, diminished ICAM-1-Ig binding was observed, suggesting that gp120-mediated activation of LFA-1 is transient (FIG. 13d). This is similar to the transient nature of MadCAM-mediated activation of LFA-1 (Dustin et al., *Annu. Rev. Immunol.,* 9: 27-66, 1991). Induction of ICAM-1-Ig binding occurred in cells cultured overnight in the absence of exogenous IL2. Cells cultured in the presence of IL2 (but no gp120), when stained with ICAM-1-Ig, showed a uniform increase in ICAM-1-Ig reactivity relative to cells cultured overnight in the absence of IL2 (FIGS. 13a and 13c), suggesting that on these cells LFA-1 is presented in an intermediate or activated conformation. When these cells were treated with gp120, no additional ICAM-1-Ig binding was observed, indicating that, in the present culture system, overnight IL2 starvation is required in order to observe gp120-mediated LFA-1 activation. Taken together these results demonstrate that gp120, and particularly trimeric gp120, rapidly induces the activation of LFA-1 on the surface of suboptimally activated (IL2-starved) CD4+ T-cells, and that this activity requires a direct interaction between gp120 and α4β7 integrin.

Example 7 gp120 Binding to α4β7 Integrin Increases the Efficiency of HIV Infection of Suboptimally Activated CD4+ T-Cells This example illustrates that α4β7 integrin increases the efficiency of HIV infection of suboptimally activated CD4+ T-cells.

The ability of gp120-α4β7 integrin-mediated activation of LFA-1 to enhance infection of CD4+ T-cells was determined. The observations that gp120 only induced activation of LFA-1 on cells starved of exogenous IL2 prompted the carrying out of single-round infection assays on suboptimally activated cells. RA-stimulated CD4+ T-cells were cultured overnight in the absence of IL2 and then infected with HIV-1 Bal. Fours hours post-infection, cells were lysed, total high-molecular weight DNA was isolated, and proviral DNA was measured by real-time PCR as previously described (Chun et al., *Proc. Natl. Acad. Sci. USA,* 100: 1908-1913, 2003). Initially, the potential of LFA-1 activation to promote infection in the present culture system was determined by comparing infection in the presence and absence of $Mn^{++}$, noting that $Mn^{++}$ increases the activation state of both α4β7 integrin and LFA-1. These studies resulted in approximately a 3-fold increase in infection in the present culture system (FIG. 14a). In the presence of $Mn^{++}$, an anti-α4 integrin mAb HP2/1, which blocks gp120-mediated activation of LFA-1 (FIG. 12), did not significantly affect infection. The effect of disrupting gp120-α4β7 integrin interactions on the efficiency of infection under conditions in which LFA-1 is not pre-activated was determined. IL2-starved cells were inoculated with Bal in the presence of either murine IgG1 or the anti α4 integrin mAb HP2/1. In studies utilizing multiple donors, an average about 2-fold reduction in infectivity was observed when HP2/1 was included in the inoculum (FIG. 14b). To further address the specific role of α4β7 integrin, it was noted that gp120-binding to α4β7 integrin on T-cells in vitro requires that those cells are first cultured in the presence of RA (FIG. 3a). Although cells cultured without RA were infected, HP2/1 produced no inhibitory effect (FIG. 14c). gp120 did not induce LFA-1 on cells in which IL2 is kept in the culture medium, and HP2/1 exhibited no inhibitory effect on the infection of these cells (FIG. 14d). It is concluded that disrupting HIV binding to α4β7 integrin reduces the efficiency with which CD4+ T-cells are infected under conditions of suboptimal activation (IL2 starvation), the same conditions required for gp120-mediated activation of LFA-1. Given the role of LFA-1 in increasing the efficiency of infection of quiescent cells (Tardif and Tremblay, *J. Virol.,* 79: 13714-24, 2005), it is likely that LFA-1 activation contributes to the increased levels of infection observed in the absence of HP2/1; however it is possible, and perhaps likely, that additional α4β7 integrin-mediated responses also play a role.

Example 8

Treatment of HIV in a Human Subject

This example describes a particular method that can be used to treat HIV in a human subject by administration of one or more agents that inhibit or reduce the activation of α4 integrin by gp120. Although particular methods, dosages, and modes of administrations are provided, one skilled in the art will appreciate that variations can be made without substantially affecting the treatment.

Based upon the teaching disclosed herein, HIV, such as HIV type 1 (HIV-1) or HIV type 2 (HIV-2), can be treated by administering a therapeutically effective amount of an agent (such as an α4-specific integrin antagonist) that specifically inhibits the activation of the α4 integrin (such as by interfering with the binding of α4 integrin with gp120) thereby reducing or eliminating the activity of α4 integrin which in turn in reduces or eliminates HIV infection, replication or a combination thereof.

Briefly, the method can include screening subjects to determine if they have HIV, such as HIV-1 or HIV-2. Subjects having HIV are selected. In one example, subjects having increased levels of HIV antibodies in their blood (as detected with an enzyme-linked immunosorbent assay, Western blot, immunofluorescence assay, or nucleic acid testing, including viral RNA or proviral DNA amplification methods are selected. In one example, a clinical trial would include half of the subjects following the established protocol for treatment of HIV (such as a highly active antiretroviral therapy). The other half would follow the established protocol for treatment of HIV (such as treatment with highly active antiretroviral compounds) in combination with administration of the agents including α4-specific integrin antagonist (as described above). In another example, a clinical trial would include half of the subjects following the established protocol for treatment of HIV (such as a highly active antiretroviral therapy). The other half would receive an agent including α4-specific integrin antagonist (such as a α4β7 or α4β7 integrin antagonist).

Screening Subjects

In particular examples, the subject is first screened to determine if they have HIV. Examples of methods that can be used to screen for HIV include a combination of measuring a subject's CD4+ T cell count and the level of HIV in serum blood levels.

In some examples, HIV testing consists of initial screening with an enzyme-linked immunosorbent assay (ELISA) to detect antibodies to HIV, such as to HIV-1. Specimens with a nonreactive result from the initial ELISA are considered HIV-negative unless new exposure to an infected partner or partner of unknown HIV status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered HIV-positive and indicative of HIV infection. Specimens that are repeatedly ELISA-reactive occasionally provide an indeterminate Western blot result, which may be either an incomplete antibody response to HIV in an infected person, or nonspecific reactions in an uninfected person. IFA can be used to confirm infection in these ambiguous cases. In some instances, a second specimen will be collected more than a month later and retested for subjects with indeterminate Western blot results. In additional examples, nucleic acid testing (e.g., viral RNA or proviral DNA amplification method) can also help diagnosis in certain situations.

The detection of HIV in a subject's blood is indicative that the subject has HIV and is a candidate for receiving the therapeutic compositions disclosed herein. Moreover, detection of a CD4+ T cell count below 350 per microliter, such as 200 cells per microliter, is also indicative that the subject is likely to have HIV.

In additional examples, screening of a subject further includes determining if the subject has multiple sclerosis or Crohn's disease by methods known to one of skill in the art. In a particular example, a subject that has HIV, but not multiple sclerosis or Crohn's disease, is a candidate for receiving one of therapeutic agents disclosed herein.

Pre-screening is not required prior to administration of the therapeutic compositions disclosed herein (such as those that include a specific α4 integrin antagonist that inhibits or reduces α4 integrin activation, including activation by gp120).

Pre-Treatment of Subjects

In particular examples, the subject is treated prior to administration of a therapeutic agent that includes one or more of the disclosed α4-specific integrin antagonists. However, such pre-treatment is not always required, and can be determined by a skilled clinician. For example, the subject can be treated with an established protocol for treatment of HIV (such as a highly active antiretroviral therapy).

Administration of Therapeutic Compositions

Following subject selection, a therapeutic effective dose of the agent including an α4-specific integrin antagonist is administered to the subject (such as an adult human or a newborn infant either at risk for contracting HIV or known to be infected with HIV). For example, a therapeutic effective dose of an agent including one or more of the α4-specific integrin antagonist is administered to the subject to reduce or inhibit α4-α4-integrin activation (such as activation by gp120). The methods can include administering an α4 integrin subunit receptor antagonist, such as an antibody, an LDV peptide, a peptidomimetic antagonist, a proteomimetic antagonist, or a small molecule antagonist (as described in detail above in the Method of Treatment Section). Additional agents, such as anti-viral agents, can also be administered to the subject simultaneously or prior to or following administration of the disclosed agents. Administration can be achieved by any method known in the art, such as oral administration, inhalation, intravenous, intramuscular, intraperitoneal, or subcutaneous.

In some particular examples, the agent is a α4β7-specific integrin antagonist. In another example, the agent is a α4β1-specific integrin antagonist. In particular examples, the agent includes an antibody, such as a monoclonal antibody, that specifically binds to a α4, β1 or β7 integrin subunit. For example, specific-α4 integrin subunit antibodies include, but are not limited to, a humanized form of HP2/1 monoclonal antibody, a humanized form of L25 monoclonal antibody, a humanized form of 2B4-3 monoclonal antibody or fragments thereof. β7 integrin subunit monoclonal antibodies can include, but are not limited to, a humanized form of FIB504 monoclonal antibody, a humanized form of FIB27 monoclonal antibody or fragments thereof. In additional examples, the α4-specific integrin antagonist is an LDV peptide, such as a cyclic hexapeptide with the amino acid sequence of CWLDVC.

The amount of the composition administered to prevent, reduce, inhibit, and/or treat HIV or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., HIV) in a subject without causing a substantial cytotoxic effect in the subject. An effective amount can be readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a daily, weekly, or monthly repeated administration protocol). In one example, therapeutic agents that include one or more α4-specific integrin antagonists are administered intravenously to a human. As such, these compositions may be formulated with an inert diluent or with an pharmaceutically acceptable carrier.

In one specific example, antibodies are administered at 5 mg per kg every two weeks or 10 mg per kg every two weeks depending upon the particular stage of HIV. In an example, the antibodies are administered continuously. In another example, antibodies or antibody fragments are administered at 50 μg per kg given twice a week for 2 to 3 weeks.

Administration of the therapeutic compositions can be taken long term (for example over a period of months or years).

Assessment

Following the administration of one or more therapies, subjects having HIV (for example, HIV-1 or HIV-2) can be monitored for reductions in HIV levels, increases in a subjects CD4+ T cell count, or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV infection, HIV replication or combination thereof. A partial response may also be an increase in CD4+ T cell count such as at least 350 T cells per microliter.

Example 9

Method of Inhibiting HIV Infection or Replication

This example illustrates the methods of inhibiting HIV infection or replication via administering an agent including α4 integrin-specific antagonists.

Based upon the teachings disclosed herein, HIV infection, replication or a combination thereof can be reduced or inhibited by contacting a cell with an effective amount of an agent including an α4-specific integrin antagonist in which the agent specifically inhibits the activation of the α4 integrin, thereby inhibiting HIV infection. The methods can also include contacting a cell with a fragment of gp120 that interferes with the interaction of gp120 and α4 integrin subunit. The methods can also include administering an α4 integrin subunit antagonist, such as an antibody, a peptide antagonist, an LDV peptide, a peptidomimetic antagonist, a proteomimetic antagonist, or a small molecule antagonist (as described in detail in Methods of Treatment Section and Example 9). The cell can also be contacted with an effective amount of an additional agent, such as anti-viral agent. The cell can be in vivo or in vitro. In a particular example, the method inhibits HIV infection or replication in gut-associated lymphoid tissue. In certain examples, the α4-specific integrin antagonists act as a microbicide, in which the antagonists reduce the infectivity of HIV.

Example 10

Screening of Agents to Treat HIV

This example describes methods that can be used to identify agents to treat HIV.

According to the teachings herein, one or more agents for treating HIV, such as HIV-1 or HIV-2, can be identified by contacting an a cell, such as a cell expressing at least one of a α4β1 or α4β7 integrin cell, with one or more test agents under conditions sufficient for the one or more test agents to alter the activity of α4 integrin. The method can also include detecting a decrease in the binding of a natural ligand of the α4β1, α4β7 or αLβ2 integrin to the α4β1 or α4β7 integrin relative to a control. For example, the natural ligand can be at least one of MadCAM-1 or VCAM-1. In a further example, the method can include contacting the cell with HIV. A decrease in the binding of the natural ligand of the α4β1 or α4β7 integrin to the α4β1 or α4β7 integrin relative to a control identifies the agent as one that is useful to treat HIV. Decreased binding can be detected by an in vitro assay in which the activity of the one or more natural ligands in the presence and absence of the one or more test agents can be determined. Various types of in vitro assays may be employed to identify agents to treat HIV including, but not limited to, HIV-infection assays, LFA-activity assays, binding assays, standard Western blot or immunoassay techniques and other well known assays to those of skill in the art. However, the disclosure is not limited to particular methods of detection.

In a specific example, a library of α4 integrin antagonists, such as LDV peptides, or peptidomimetic, proteomimetic or small molecule α4 integrin antagonists are screened for their effect on gp120 activation of α4 integrin. Regardless of the assay technique, agents that cause at least a 2-fold decrease, such as at least a 3-fold decrease, at least a 4-fold decrease, or at least a 5-fold decrease in the activity, such as binding of gp120 to α4 integrin, are selected for further evaluation.

Potential therapeutic agents identified with these or other approaches, including the specific assays and screening systems described herein, are used as lead compounds to identify other agents having even greater modulatory effects on α4 integrin. Candidate agents also can be tested in additional cell lines and animal models of HIV to determine their therapeutic value. The agents also can be tested for safety in animals, and then used for clinical trials in animals or humans. In one example, genetically engineered mouse models of HIV are employed to determine therapeutic value of test agents. In another example, simian immunodeficiency virus (SIV)-macaque or a chimeric simian-human immunodeficiency virus (SHIV)-macaque model are utilized. SHIV strains have the viral envelope of HIV but the gag/pol genes of SIV. Pathogenesis is similar with respect to macrophage and T lymphocyte cell tropism, histopathologic changes, CD4-cell depletion and clinical signs of auto-immune deficiency syndrome (AIDS) in virulent strains.

It will be apparent that the precise details of the methods or compositions described may be varied or modified without departing from the spirit of the described invention. We claim all such modifications and variations that fall within the scope and spirit of the claims below.

The invention claimed is:

1. A method for the treatment of a subject infected with human immunodeficiency virus (HIV), comprising:
   selecting the subject who is infected with HIV; and
   administering to the subject a therapeutically effective amount of an α4β7 monoclonal antibody which specifically inhibits binding of a LDV sequence in a gp 120 V2 loop to an α4β7 integrin heterodimer, thereby treating the subject with HIV.

2. The method of claim 1, wherein the monoclonal antibody is a β7 integrin subunit monoclonal antibody.

3. The method of claim 2, wherein the β7 integrin subunit monoclonal antibody is a humanized form of FIB504 monoclonal antibody, humanized form of FIB27 monoclonal antibody or fragments thereof.

4. The method of claim 1, wherein the HIV is HIV type 1 (HIV-1).

5. The method of claim 1, wherein the HIV is HIV type 2 (HIV-2).

6. The method of claim 1, wherein the antibody is not natalizumab.

7. The method of claim 1, wherein the subject does not have multiple sclerosis or Crohn's disease.

8. The method of claim 1, wherein the subject is a newborn infant.

9. The method of claim 1, wherein the α4β7 monoclonal antibody is MLN02.

10. The method of claim 1, wherein the α4β7 monoclonal antibody is administered with an additional agent.

11. The method of claim 10, wherein the additional agent is an anti-viral agent.

12. The method of claim 1, wherein the α4β7 monoclonal antibody is a human α4β7 monoclonal antibody.

* * * * *

```
                              SEQUENCE LISTING

<160> NUMBER OF SEQ ID NOS: 35

<210> SEQ ID NO 1
    <211> LENGTH: 6
    <212> TYPE: PRT
    <213> ORGANISM: Artificial sequence
    <220> FEATURE:
    <223> OTHER INFORMATION: synthetic peptide integrin antagonist

<400> SEQUENCE: 1

Cys Trp Leu Asp Val Cys
    1               5

<210> SEQ ID NO 2
    <211> LENGTH: 22
    <212> TYPE: DNA
    <213> ORGANISM: Artificial sequence
    <220> FEATURE:
    <223> OTHER INFORMATION: oligonucleotide primer

<400> SEQUENCE: 2
ggtctctctg gttagaccag at                                              22

<210> SEQ ID NO 3
    <211> LENGTH: 22
    <212> TYPE: DNA
    <213> ORGANISM: Artificial sequence
    <220> FEATURE:
    <223> OTHER INFORMATION: oligonucleotide primer

<400> SEQUENCE: 3
ctgctagaga ttttccacac tg                                              22

<210> SEQ ID NO 4
    <211> LENGTH: 21
    <212> TYPE: DNA
    <213> ORGANISM: Artificial sequence
    <220> FEATURE:
    <223> OTHER INFORMATION: oligonucleotide probe

<400> SEQUENCE: 4
agtagtgtgt gcccgtctgt t                                               21
```

```
<210> SEQ ID NO 5
<211> LENGTH: 25
<212> TYPE: PRT
<213> ORGANISM: Artificial sequence
<220> FEATURE:
<223> OTHER INFORMATION: synthetic peptide integrin antagonist

<400> SEQUENCE: 5

Asp Glu Leu Pro Gln Leu Val Thr Leu Pro His Pro Asn Leu His Gly
1               5                   10                  15

Pro Glu Ile Leu Asp Val Pro Ser Thr
            20                  25

<210> SEQ ID NO 6
<211> LENGTH: 9
<212> TYPE: PRT
<213> ORGANISM: Artificial sequence
<220> FEATURE:
<223> OTHER INFORMATION: synthetic peptide integrin antagonist

<400> SEQUENCE: 6

Asp Glu Leu Pro Gln Leu Val Thr Leu
1               5

<210> SEQ ID NO 7
<211> LENGTH: 12
<212> TYPE: PRT
<213> ORGANISM: Artificial sequence
<220> FEATURE:
<223> OTHER INFORMATION: synthetic peptide integrin antagonist

<400> SEQUENCE: 7

Leu His Gly Pro Glu Ile Leu Asp Val Pro Ser Thr
1               5                   10

<210> SEQ ID NO 8
<211> LENGTH: 10
<212> TYPE: PRT
<213> ORGANISM: Artificial sequence
<220> FEATURE:
<223> OTHER INFORMATION: synthetic peptide integrin antagonist

<400> SEQUENCE: 8

Gly Pro Glu Ile Leu Asp Val Pro Ser Thr
1               5                   10

<210> SEQ ID NO 9
<211> LENGTH: 14
<212> TYPE: PRT
<213> ORGANISM: Artificial sequence
<220> FEATURE:
<223> OTHER INFORMATION: synthetic peptide integrin antagonist

<400> SEQUENCE: 9

Val Thr Leu Pro His Pro Asn Leu His Gly Pro Glu Ile Leu
1               5                   10

<210> SEQ ID NO 10
<211> LENGTH: 19
<212> TYPE: PRT
<213> ORGANISM: Artificial sequence
<220> FEATURE:
<223> OTHER INFORMATION: synthetic peptide integrin antagonist

<400> SEQUENCE: 10

Val Thr Leu Pro His Pro Asn Leu His Gly Pro Glu Ile Leu Asp Val
1               5                   10                  15
```

Pro Ser Thr

<210> SEQ ID NO 11
<211> LENGTH: 8
<212> TYPE: PRT
<213> ORGANISM: Artificial sequence
<220> FEATURE:
<223> OTHER INFORMATION: synthetic peptide integrin antagonist

<400> SEQUENCE: 11

Glu Ile Leu Asp Val Pro Ser Thr
1               5

<210> SEQ ID NO 12
<211> LENGTH: 6
<212> TYPE: PRT
<213> ORGANISM: Artificial sequence
<220> FEATURE:
<223> OTHER INFORMATION: synthetic peptide integrin antagonist

<400> SEQUENCE: 12

Leu Asp Val Pro Ser Thr
1               5

<210> SEQ ID NO 13
<211> LENGTH: 5
<212> TYPE: PRT
<213> ORGANISM: Artificial sequence
<220> FEATURE:
<223> OTHER INFORMATION: synthetic peptide integrin antagonist

<400> SEQUENCE: 13

Glu Ile Leu Asp Val
1               5

<210> SEQ ID NO 14
<211> LENGTH: 5
<212> TYPE: PRT
<213> ORGANISM: Artificial sequence
<220> FEATURE:
<223> OTHER INFORMATION: synthetic peptide integrin antagonist

<400> SEQUENCE: 14

Leu Asp Val Pro Ser
1               5

<210> SEQ ID NO 15
<211> LENGTH: 3
<212> TYPE: PRT
<213> ORGANISM: Artificial sequence
<220> FEATURE:
<223> OTHER INFORMATION: synthetic peptide integrin antagonist

<400> SEQUENCE: 15

Leu Asp Val
1

<210> SEQ ID NO 16
<211> LENGTH: 20
<212> TYPE: PRT
<213> ORGANISM: Artificial sequence
<220> FEATURE:
<223> OTHER INFORMATION: synthetic peptide integrin antagonist

<400> SEQUENCE: 16

Asp Glu Leu Pro Gln Leu Val Thr Leu Pro His Pro Asn Leu His Gly

```
1               5                   10                  15

Pro Glu Ile Leu
            20

<210> SEQ ID NO 17
<211> LENGTH: 7
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: MISC_FEATURE
<222> LOCATION: (4)..(4)
<223> OTHER INFORMATION: Xaa is D-proline

<400> SEQUENCE: 17

Leu Thr Gly Xaa Leu Asp Ile
1               5

<210> SEQ ID NO 18
<211> LENGTH: 6
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (3)..(3)
<223> OTHER INFORMATION: Xaa is D-proline

<400> SEQUENCE: 18

Thr Gly Xaa Leu Asp Ile
1               5

<210> SEQ ID NO 19
<211> LENGTH: 5
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (2)..(2)
<223> OTHER INFORMATION: Xaa is D-proline

<400> SEQUENCE: 19

Gly Xaa Leu Asp Ile
1               5

<210> SEQ ID NO 20
<211> LENGTH: 4
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa is D-proline

<400> SEQUENCE: 20

Xaa Leu Asp Ile
1

<210> SEQ ID NO 21
<211> LENGTH: 6
<212> TYPE: PRT
<213> ORGANISM: Artificial sequence
<220> FEATURE:
```

```
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa is D-cysteine
<220> FEATURE:
<221> NAME/KEY: misc_feature
<222> LOCATION: (6)..(6)
<223> OTHER INFORMATION: Xaa is D-cysteine

<400> SEQUENCE: 21

Xaa Met Leu Asp Ile Xaa
1               5

<210> SEQ ID NO 22
<211> LENGTH: 6
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa is D-cysteine
<220> FEATURE:
<221> NAME/KEY: misc_feature
<222> LOCATION: (6)..(6)
<223> OTHER INFORMATION: Xaa is D-cysteine

<400> SEQUENCE: 22

Xaa Leu Leu Asp Ile Xaa
1               5

<210> SEQ ID NO 23
<211> LENGTH: 5
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa is D-cysteine
<220> FEATURE:
<221> NAME/KEY: misc_feature
<222> LOCATION: (5)..(5)
<223> OTHER INFORMATION: Xaa is D-cysteine

<400> SEQUENCE: 23

Xaa Asn Leu Asp Xaa
1               5

<210> SEQ ID NO 24
<211> LENGTH: 6
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa is D-cysteine
<220> FEATURE:
<221> NAME/KEY: misc_feature
<222> LOCATION: (6)..(6)
<223> OTHER INFORMATION: Xaa is D-cysteine

<400> SEQUENCE: 24

Xaa Tyr Leu Asp Ile Xaa
1               5
```

```
<210> SEQ ID NO 25
<211> LENGTH: 7
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa is D-cysteine
<220> FEATURE:
<221> NAME/KEY: misc_feature
<222> LOCATION: (7)..(7)
<223> OTHER INFORMATION: Xaa is D-cysteine

<400> SEQUENCE: 25

Xaa Gly Tyr Leu Asp Ile Xaa
1               5

<210> SEQ ID NO 26
<211> LENGTH: 7
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa is D-cysteine
<220> FEATURE:
<221> NAME/KEY: misc_feature
<222> LOCATION: (7)..(7)
<223> OTHER INFORMATION: Xaa is D-cysteine

<400> SEQUENCE: 26

Xaa Ala Trp Leu Asp Ile Xaa
1               5

<210> SEQ ID NO 27
<211> LENGTH: 7
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa is D-cysteine
<220> FEATURE:
<221> NAME/KEY: misc_feature
<222> LOCATION: (7)..(7)
<223> OTHER INFORMATION: Xaa is D-cysteine

<400> SEQUENCE: 27

Xaa Leu Asp Ile Gly Asp Xaa
1               5

<210> SEQ ID NO 28
<211> LENGTH: 7
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa is D-cysteine
<220> FEATURE:
<221> NAME/KEY: misc_feature
<222> LOCATION: (7)..(7)
<223> OTHER INFORMATION: Xaa is D-cysteine

<400> SEQUENCE: 28
```

Xaa Leu Asp Ile His Pro Xaa
1               5

<210> SEQ ID NO 29
<211> LENGTH: 5
<212> TYPE: PRT
<213> ORGANISM: Artificial sequence
<220> FEATURE:
<223> OTHER INFORMATION: synthetic peptide integrin antagonist

<400> SEQUENCE: 29

Cys Leu Asp Thr Cys
1               5

<210> SEQ ID NO 30
<211> LENGTH: 6
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (5)..(5)
<223> OTHER INFORMATION: Xaa is D-proline

<400> SEQUENCE: 30

Leu Asp Thr Ala Xaa Ala
1               5

<210> SEQ ID NO 31
<211> LENGTH: 5
<212> TYPE: PRT
<213> ORGANISM: Artificial sequence
<220> FEATURE:
<223> OTHER INFORMATION: synthetic peptide integrin antagonist

<400> SEQUENCE: 31

Cys Asp Leu Trp Cys
1               5

<210> SEQ ID NO 32
<211> LENGTH: 40
<212> TYPE: PRT
<213> ORGANISM: homo sapiens

<400> SEQUENCE: 32

Cys Ser Phe Asn Ile Ser Thr Ser Ile Arg Gly Lys Val Gln Lys Glu
1               5                   10                  15

Tyr Ala Phe Phe Tyr Lys Leu Asp Ile Ile Pro Ile Asp Asn Asp Thr
            20                  25                  30

Thr Ser Tyr Ser Leu Thr Ser Cys
        35                  40

<210> SEQ ID NO 33
<211> LENGTH: 39
<212> TYPE: PRT
<213> ORGANISM: Artificial sequence
<220> FEATURE:
<223> OTHER INFORMATION: consensus sequence for all V2 loops of HXB2
      HIV-1

<400> SEQUENCE: 33

Cys Ser Phe Asn Ile Thr Thr Glu Ile Arg Asp Lys Lys Lys Lys Val
1               5                   10                  15

Tyr Ala Leu Phe Tyr Lys Leu Asp Val Val Pro Ile Asp Asp Asn Asn

-continued

```
                    20                  25                  30
Ser Tyr Arg Leu Ile Asn Cys
        35

<210> SEQ ID NO 34
<211> LENGTH: 5
<212> TYPE: PRT
<213> ORGANISM: Artificial sequence
<220> FEATURE:
<223> OTHER INFORMATION: synthetic peptide integrin antagonist
<220> FEATURE:
<221> NAME/KEY: misc_feature
<222> LOCATION: (1)..(1)
<223> OTHER INFORMATION: Xaa can be any D amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 34

Xaa Leu Asp Val Xaa
1               5

<210> SEQ ID NO 35
<211> LENGTH: 4
<212> TYPE: PRT
<213> ORGANISM: Artificial sequence
<220> FEATURE:
<223> OTHER INFORMATION: synthetic peptide integrin antagonist

<400> SEQUENCE: 35

Leu Glu Asp Val
1
```